(12) United States Patent
Huang et al.

(10) Patent No.: US 12,408,846 B2
(45) Date of Patent: Sep. 9, 2025

(54) ESTIMATION DEVICE, ESTIMATION SYSTEM, ESTIMATION METHOD, AND PROGRAM RECORDING MEDIUM

(71) Applicant: NEC Corporation, Tokyo (JP)

(72) Inventors: Chenhui Huang, Tokyo (JP); Kenichiro Fukushi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 17/783,314

(22) PCT Filed: Dec. 25, 2019

(86) PCT No.: PCT/JP2019/050864
§ 371 (c)(1),
(2) Date: Jun. 8, 2022

(87) PCT Pub. No.: WO2021/130907
PCT Pub. Date: Jul. 1, 2021

(65) Prior Publication Data
US 2023/0009480 A1 Jan. 12, 2023

(51) Int. Cl.
| A61B 5/11 | (2006.01) |
| A43B 3/44 | (2022.01) |
| A61B 5/00 | (2006.01) |
| G01P 3/00 | (2006.01) |
| G01P 15/08 | (2006.01) |
| G01P 15/18 | (2013.01) |

(52) U.S. Cl.
CPC .............. *A61B 5/112* (2013.01); *A43B 3/44* (2022.01); *A61B 5/6807* (2013.01); *G01P 3/00* (2013.01); *G01P 15/08* (2013.01); *G01P 15/18* (2013.01)

(58) Field of Classification Search
CPC ....... A61B 5/112; A81B 5/6807; G01P 15/08; G01P 15/18; G01P 3/00; A43B 3/44
See application file for complete search history.

(56) References Cited

U.S. PATENT DOCUMENTS

| 8,751,320 B1 * | 6/2014 | Kemist | G06Q 30/06 |
| | | | 705/26.1 |
| 2006/0120564 A1 * | 6/2006 | Imagawa | G06V 40/20 |
| | | | 382/103 |
| 2008/0203144 A1 | 8/2008 | Kim | |
| 2010/0170116 A1 * | 7/2010 | Shim | A43B 7/082 |
| | | | 36/3 R |

(Continued)

FOREIGN PATENT DOCUMENTS

| JP | 2007-263918 A | 10/2007 |
| JP | 2010-218177 A | 9/2010 |

(Continued)

OTHER PUBLICATIONS

Translation of JP2019-005340.*

(Continued)

*Primary Examiner* — Helen C Kwok
(74) *Attorney, Agent, or Firm* — Sughrue Mion, PLLC

(57) ABSTRACT

An estimation device that includes an extraction unit that acquires sensor data from a sensor installed on footwear and extracts a gait feature quantity characteristic of walking in the footwear by using the sensor data, and an estimation unit that estimates a type of the footwear based on the gait feature quantity extracted by the extraction unit.

9 Claims, 24 Drawing Sheets

(56) References Cited

U.S. PATENT DOCUMENTS

| | | | | |
|---|---|---|---|---|
| 2013/0218297 | A1* | 8/2013 | Nordman, Jr. | A61F 2/66 |
| | | | | 623/53 |
| 2016/0081435 | A1* | 3/2016 | Marks | A43D 1/02 |
| | | | | 382/154 |
| 2016/0147841 | A1 | 5/2016 | Gray et al. | |
| 2016/0180440 | A1* | 6/2016 | Dibenedetto | G06Q 30/02 |
| | | | | 705/26.7 |
| 2016/0220153 | A1* | 8/2016 | Annegarn | A61B 5/7275 |
| 2016/0367199 | A1* | 12/2016 | Stefanyshyn | A61B 5/1038 |
| 2017/0068774 | A1* | 3/2017 | Cluckers | A61B 5/743 |
| 2017/0161564 | A1* | 6/2017 | Jobling | G06V 20/53 |
| 2017/0213095 | A1 | 7/2017 | Li | |
| 2017/0224048 | A1 | 8/2017 | Nagano et al. | |
| 2017/0354348 | A1* | 12/2017 | Winter | G06F 30/20 |
| 2018/0020950 | A1* | 1/2018 | Finch | A61B 5/1124 |
| | | | | 600/595 |
| 2020/0364935 | A1* | 11/2020 | Revkov | A43D 1/025 |
| 2021/0012403 | A1* | 1/2021 | Fischgrund | G06N 20/00 |
| 2021/0085034 | A1* | 3/2021 | Bischoff | G06T 7/0012 |
| 2021/0182298 | A1* | 6/2021 | Gray | G06F 16/248 |
| 2022/0335477 | A1* | 10/2022 | Oumnia | G06Q 30/0255 |
| 2022/0338735 | A1* | 10/2022 | Oumnia | A61B 5/112 |
| 2023/0009480 | A1 | 1/2023 | Huang et al. | |
| 2024/0081684 | A1 | 3/2024 | Huang et al. | |
| 2024/0081685 | A1 | 3/2024 | Huang et al. | |
| 2024/0081686 | A1 | 3/2024 | Huang et al. | |

FOREIGN PATENT DOCUMENTS

| | | | |
|---|---|---|---|
| JP | 2012-168647 A | | 9/2012 |
| JP | 2013-068455 A | | 4/2013 |
| JP | 5724237 B2 | | 5/2015 |
| JP | 2016-059795 A | | 4/2016 |
| JP | 2017-023689 | * | 2/2017 |
| JP | 2019-005340 | * | 1/2019 |
| JP | 2019-118654 A | | 7/2019 |
| KR | 2016-0131823 | * | 11/2016 |
| WO | 2018/164157 A1 | | 9/2018 |

OTHER PUBLICATIONS

Translation of KR2016-0131823.*
International Search Report for PCT Application No. PCT/JP2019/050864, mailed on Mar. 17, 2020.
English translation of Written opinion for PCT Application No. PCT/JP2019/050864, mailed on Mar. 17, 2020.
Hiroto Mitake et al., "A Method for Estimating Road Surface Condition Using Footsteps, Multimedia, Distributed. Cooperative, and Mobile" (DICOMO2018) Symposium, IPSJ Symposium Series, vol. 2018, No. 1 [CD-ROM] IPSJ Symposium Series, Jul. 4, 2018, p. 999 to p. 1007, sections 1, 2.2, 4.1.
Miyuki Fukushima et al., "An experimental study on the classification of the footstep attribute using a vibration sensor", IEICE Technical Report, vol. 116, No. 54 IEICE Technical Report, May 13, 2016. p. 19 to p. 23 section 5.3.
US Office Action for U.S. Appl. No. 18/517,060, mailed on Oct. 16, 2024.
US Office Action for U.S. Appl. No. 18/515,455, mailed on Oct. 15, 2024.

* cited by examiner

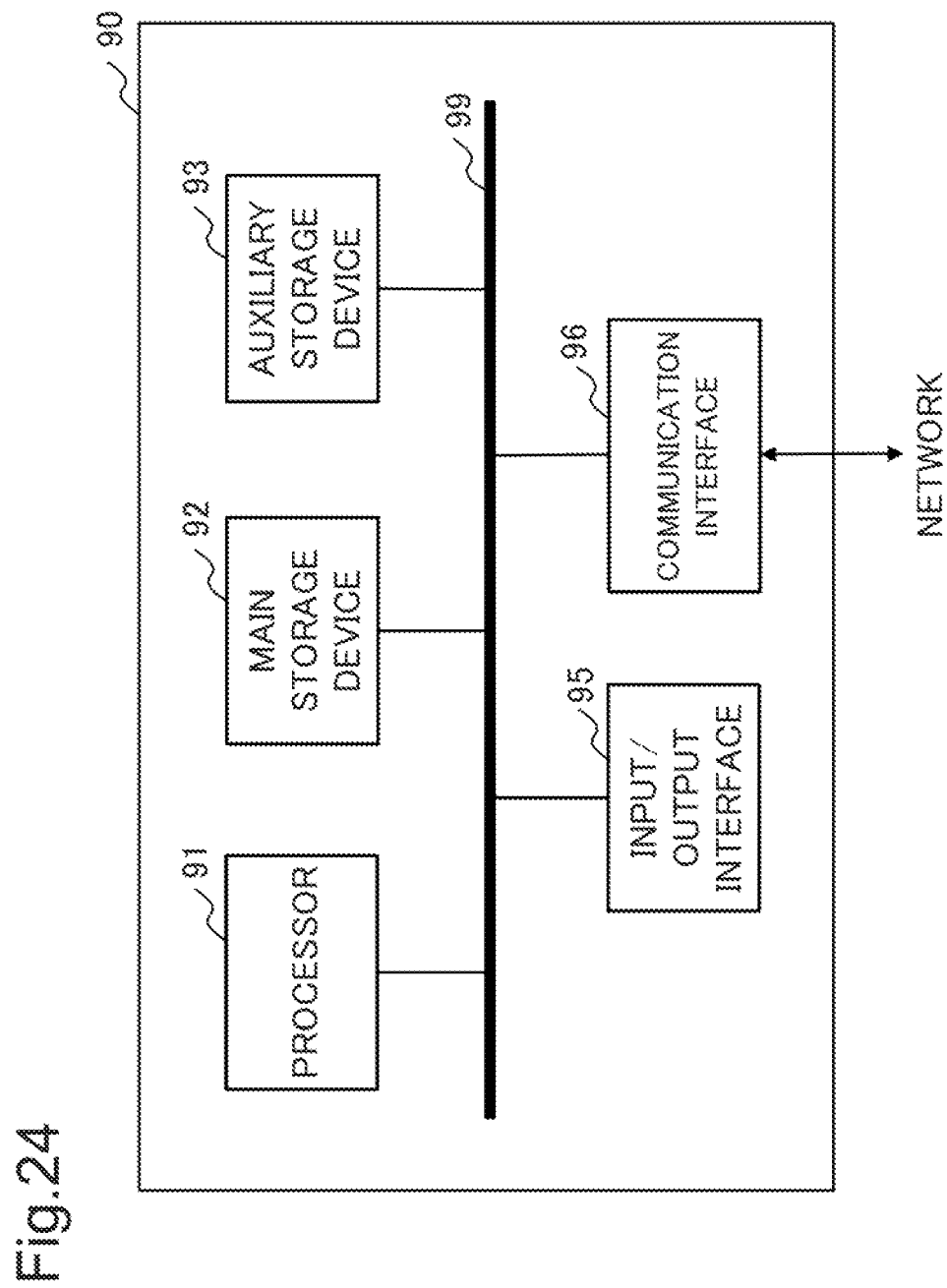

ESTIMATION DEVICE, ESTIMATION SYSTEM, ESTIMATION METHOD, AND PROGRAM RECORDING MEDIUM

This application is a National Stage Entry of PCT/JP2019/050864 filed on Dec. 25, 2019, the contents of all of which are incorporated herein by reference, in their entirety.

TECHNICAL FIELD

The present invention relates to an estimation device or the like that estimates the type of footwear worn by a pedestrian.

BACKGROUND ART

With an increase in interest in healthcare and beauty for managing a physical condition, a service that measures a gait including a gait feature of a pedestrian and provides information relevant to the gait to a user has attracted attention. The gait feature varies depending on the footwear worn by the pedestrian. For example, there is a difference in gait feature between the case of walking with exercise shoes and the case of walking with high heels.

PTL 1 discloses a gait change determination device which is mounted with an acceleration sensor and determines a change in a gait of a user based on detected acceleration. The device of PTL 1 determines the degree of temporal change of the trajectory of a portion attached with the device during walking based on the acceleration detected by the acceleration sensor.

PTL 2 discloses a method of acquiring sole pressure data from a sensor provided in an insole of a shoe, analyzing the acquired data, and acquiring a parameter regarding walking during walking or at rest.

PTL 3 discloses a sensor control device that controls a function according to a vibration given by walking of a person or the like.

CITATION LIST

Patent Literature

[PTL 1] Japanese Patent No. 5724237
[PTL 2] WO 2018/164157 A
[PTL 3] JP 2013-068455 A

SUMMARY OF INVENTION

Technical Problem

When the pedestrian is attached with the device of PTL 1, it is possible to determine a change in a gait of the user by analyzing the trajectory of a portion attached with the device during walking. However, in the method of PTL 1, the type of footwear worn by the pedestrian cannot be estimated although the change in a gait can be determined.

According to the method of PTL 2, the daily gait state of the pedestrian can be collected. However, in the method of PTL 2, the gait state of the pedestrian cannot be collected unless a sensor capable of measuring a sole pressure is installed on the footwear. Therefore, the method of PTL 2 cannot estimate the type of footwear worn by the pedestrian.

According to the method of PTL 3, a moving body which is a vibration source can be specified according to the vibration acquired by a vibration sensor mounted on an electrical appliance or the like. In the method of PTL 3, since a floor vibration waveform is used, only the state of a sole can be verified, and for example, the heel height or the like of the footwear cannot be measured. Therefore, the method of PTL 3 cannot estimate the type of footwear worn by the pedestrian.

An object of the present invention is to provide an estimation device and the like capable of estimating the type of footwear worn by a pedestrian.

Solution to Problem

An estimation device according to one aspect of the present invention includes: an extraction unit that acquires sensor data from a sensor installed on footwear and extract a gait feature quantity characteristic of walking in the footwear by using the sensor data; and an estimation unit that estimates a type of the footwear based on the gait feature quantity extracted by the extraction unit.

In an estimation method according to an aspect of the present invention, a computer performs the method including: acquiring sensor data from a sensor installed on footwear; extract a gait feature quantity characteristic of walking in the footwear by using the sensor data; and estimating a type of the footwear based on the extracted gait feature quantity.

A program according to one aspect of the present invention causes a computer to execute a process including: acquiring sensor data from a sensor installed on footwear; extract a gait feature quantity characteristic of walking in the footwear by using the sensor data; and estimating a type of the footwear based on the extracted gait feature quantity.

Advantageous Effects of Invention

According to the present invention, it is possible to provide an estimation device and the like capable of estimating the type of footwear worn by the pedestrian.

BRIEF DESCRIPTION OF DRAWINGS

FIG. 24 is a block diagram for describing an example of a hardware configuration for achieving the estimation device of the estimation system according to the example embodiment.

EXAMPLE EMBODIMENT

Figure 1:
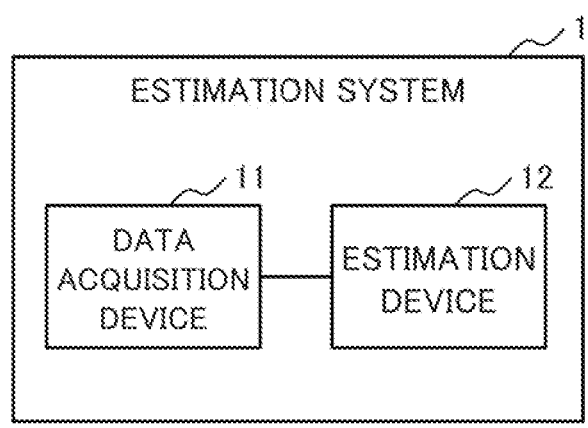
FIG. 1 is a block diagram illustrating an example of a configuration of an estimation system according to an example embodiment.

Hereinafter, an example embodiment of the present invention will be described with reference to the drawings. However, the example embodiment described below have technically preferable limitations for carrying out the present invention, but the scope of the invention is not limited to the following. In all the drawings used in the following description of the following example embodiment, the same reference numerals are given to the same parts unless there is a particular reason.

In the following example embodiment, repeated description of similar configurations and operations may be omitted.

Example Embodiment

First, an estimation system according to the example embodiment will be described with reference to the drawings. The estimation system of the present example embodiment estimates the type of footwear worn by a pedestrian by using sensor data acquired by a sensor installed in the footwear such as shoes or high heels. In the following description, a heel height indicates the relative height of a heel with respect to the footrest portion of a sole or the back side of a toe. In the measurement scene described in the present example embodiment, the heel height may indicate the height of the heel with respect to the ground. In the present example embodiment, an example will be mainly described in which the type of footwear is estimated based on a gait feature for each type of footwear having different heel heights. However, the method of the present example embodiment can be applied to the estimation of an arbitrary type of footwear as long as a gait feature portion appearing in wearing the footwear is extracted.

(Configuration)

FIG. 1 is a block diagram illustrating an example of a configuration of an estimation system 1 according to the present example embodiment. As illustrated in FIG. 1, the estimation system 1 includes a data acquisition device 11 and an estimation device 12. The data acquisition device 11 and the estimation device 12 may be connected by wire or may be connected wirelessly. The data acquisition device 11 and the estimation device 12 may be configured by a single device. The data acquisition device 11 may be excluded from the configuration of the estimation system 1, and only the estimation device 12 may configure the estimation system 1.

The data acquisition device 11 includes at least an acceleration sensor and an angular velocity sensor. For example, the data acquisition device 11 is installed on the footwear. The data acquisition device 11 converts physical quantities such as acceleration and an angular velocity acquired by the acceleration sensor and the angular velocity sensor into digital data (also referred to as sensor data), and transmits the converted sensor data to the estimation device 12.

The data acquisition device 11 is achieved by, for example, an inertial measurement device including the acceleration sensor and the angular velocity sensor. An example of the inertial measurement device includes an inertial measurement unit (IMU). The IMU includes a three-axis acceleration sensor and a three-axis angular velocity sensor. Examples of the inertial measurement device include a vertical gyro (VG), an attitude heading (AHRS), and a global positioning system/an inertial navigation system (GPS/INS).

The sensor data such as acceleration and angular velocity acquired by the data acquisition device 11 is also referred to as a gait parameter. The velocity and angle calculated by integrating the acceleration and the angular velocity are also included in the gait parameter. In the present example embodiment, a lateral direction of the pedestrian is an X direction (a right side is positive), a traveling direction of the pedestrian is a Y direction (a front side is positive), and a gravity direction is a Z direction (an upper side is positive). In the present example embodiment, rotation around the X axis is defined as roll, rotation around the Y axis is defined as pitch, and rotation around the Z axis is defined as yaw.

Figure 2:
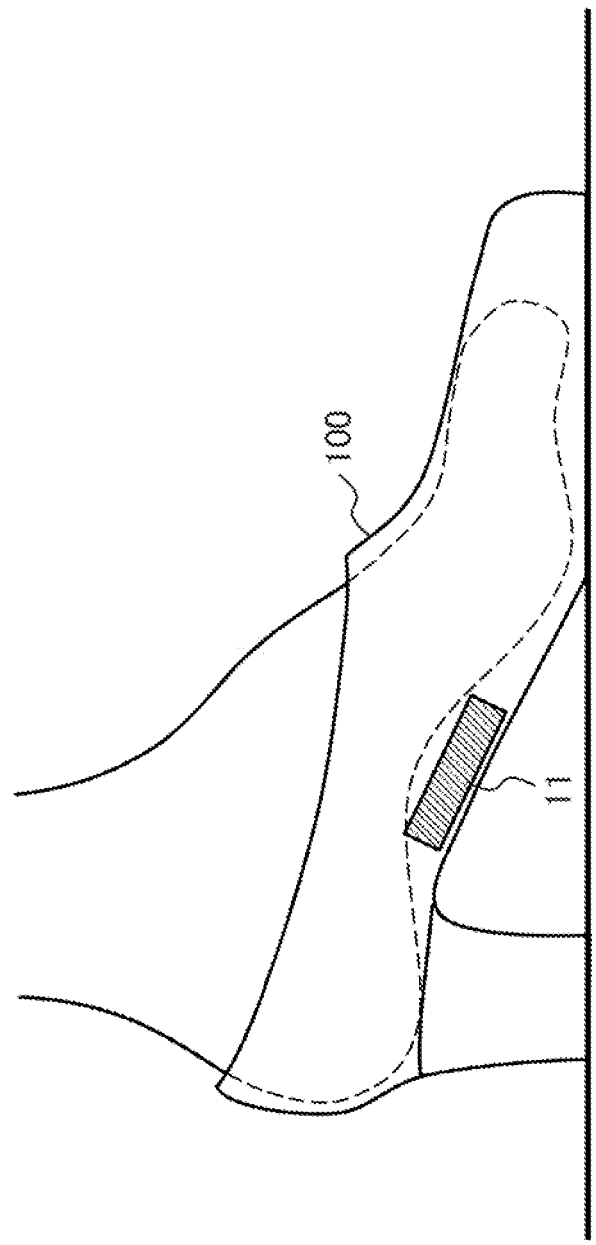
FIG. 2 is a conceptual diagram illustrating an example in which a data acquisition device of the estimation system according to the example embodiment is installed in footwear.

FIG. 2 is a conceptual diagram illustrating an example in which the data acquisition device 11 is installed in a high-heeled footwear 100. FIG. 2 illustrates an example in which the data acquisition device 11 is installed at a position facing the back side of the arch of a foot. The position where the data acquisition device 11 is installed may be a position other than the back side of the arch of the foot as long as the position is inside or on the surface of the footwear 100. For example, the data acquisition device 11 may be installed on the back side of a toe or a heel.

Figure 3:
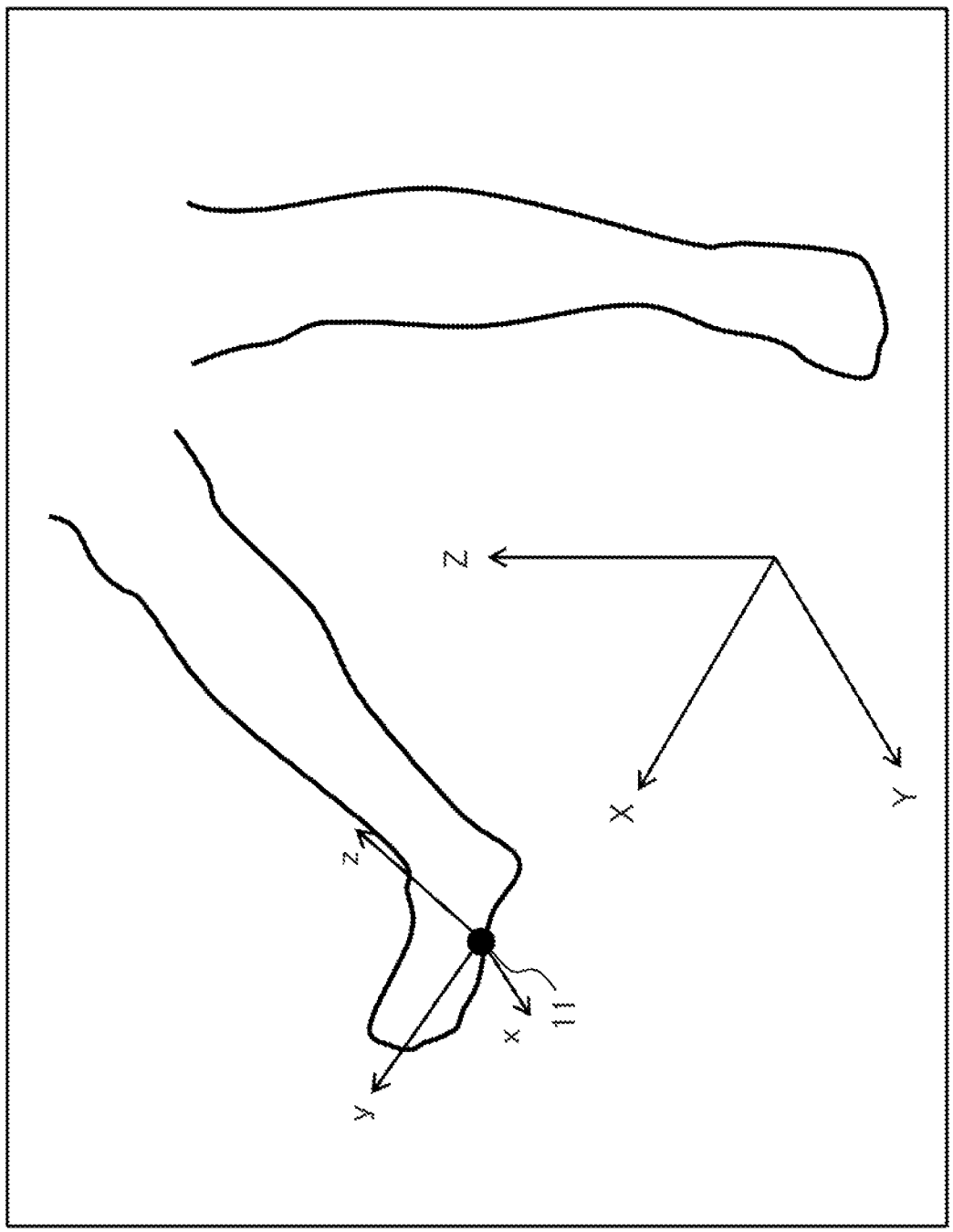
FIG. 3 is a conceptual diagram for describing a relationship between a local coordinate system and a world coordinate system of the data acquisition device of the estimation system according to the example embodiment.

FIG. 3 is a conceptual diagram for describing a local coordinate system (x-axis, y-axis, z-axis) set in the data acquisition device 11 and a world coordinate system (X axis, Y axis, Z axis) set with respect to the ground in a case where the data acquisition device 11 is installed on the back side of the arch of the foot. In the world coordinate system (X axis, Y axis, Z axis), in a state where the pedestrian is standing upright, the lateral direction of the pedestrian is set to an X-axis direction (a rightward direction is positive), a forward direction of the pedestrian (traveling direction) is set to a Y-axis direction (a forward direction is positive), and the gravity direction is set to a Z-axis direction (a vertically upward direction is positive). In a state where the pedestrian is standing upright, the local coordinate system (x-axis, y-axis, z-axis) and the world coordinate system (X axis, Y axis, Z axis) coincide with each other. When the pedestrian walks, the spatial posture of the data acquisition device 11 changes, and thus, the local coordinate system (x-axis, y-axis, z-axis) and the world coordinate system (X axis, Y axis, Z axis) are inconsistent. Therefore, the estimation device 12 converts the sensor data acquired by the data acquisition device 11 from the local coordinate system (x-axis, y-axis, z-axis) of the data acquisition device 11 into the world coordinate system (X axis, Y axis, Z axis).

Figure 4:
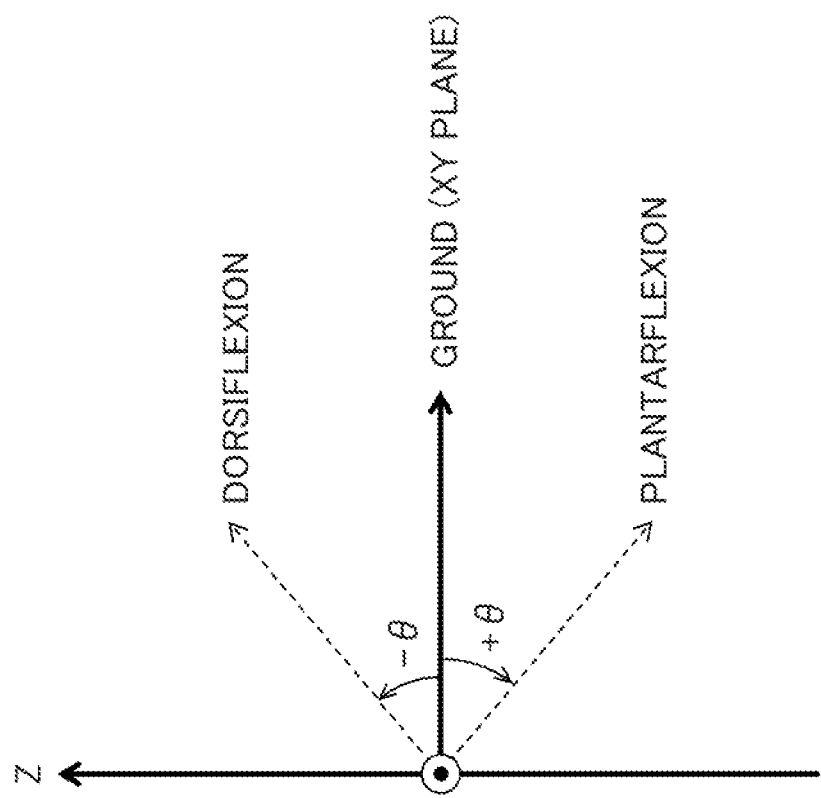
FIG. 4 is a conceptual diagram for describing a sole angle calculated by the estimation device of the estimation system according to the example embodiment.

FIG. 4 is a conceptual diagram for describing a sole angle calculated by the estimation device 12. The sole angle is the angle of the sole relative to the ground (XY plane). In the sole angle, a state in which the toe is directed upward (dorsiflexion) is defined as minus, and a state in which the toe is directed downward (plantarflexion) is defined as plus.

For example, the estimation device 12 calculates the sole angle by using the magnitude of the acceleration in each axial direction of the X axis and the Y axis. For example, by integrating the value of the angular velocity having each of the X axis, the Y axis, and the Z axis as a central axis, the estimation device 12 can calculate the sole angle around each axis. The acceleration data and the angular velocity data include high-frequency and low-frequency noises that change in various directions. Therefore, by applying a low-pass filter and a high-pass filter to the acceleration data and the angular velocity data to remove a high-frequency component and a low-frequency component, it is possible to improve the accuracy of sensor data from a foot portion where noise easily interferes. By applying a complementary filter to each of the acceleration data and the angular velocity data and taking a weighted average, the accuracy of sensor data can be improved.

Figure 5:
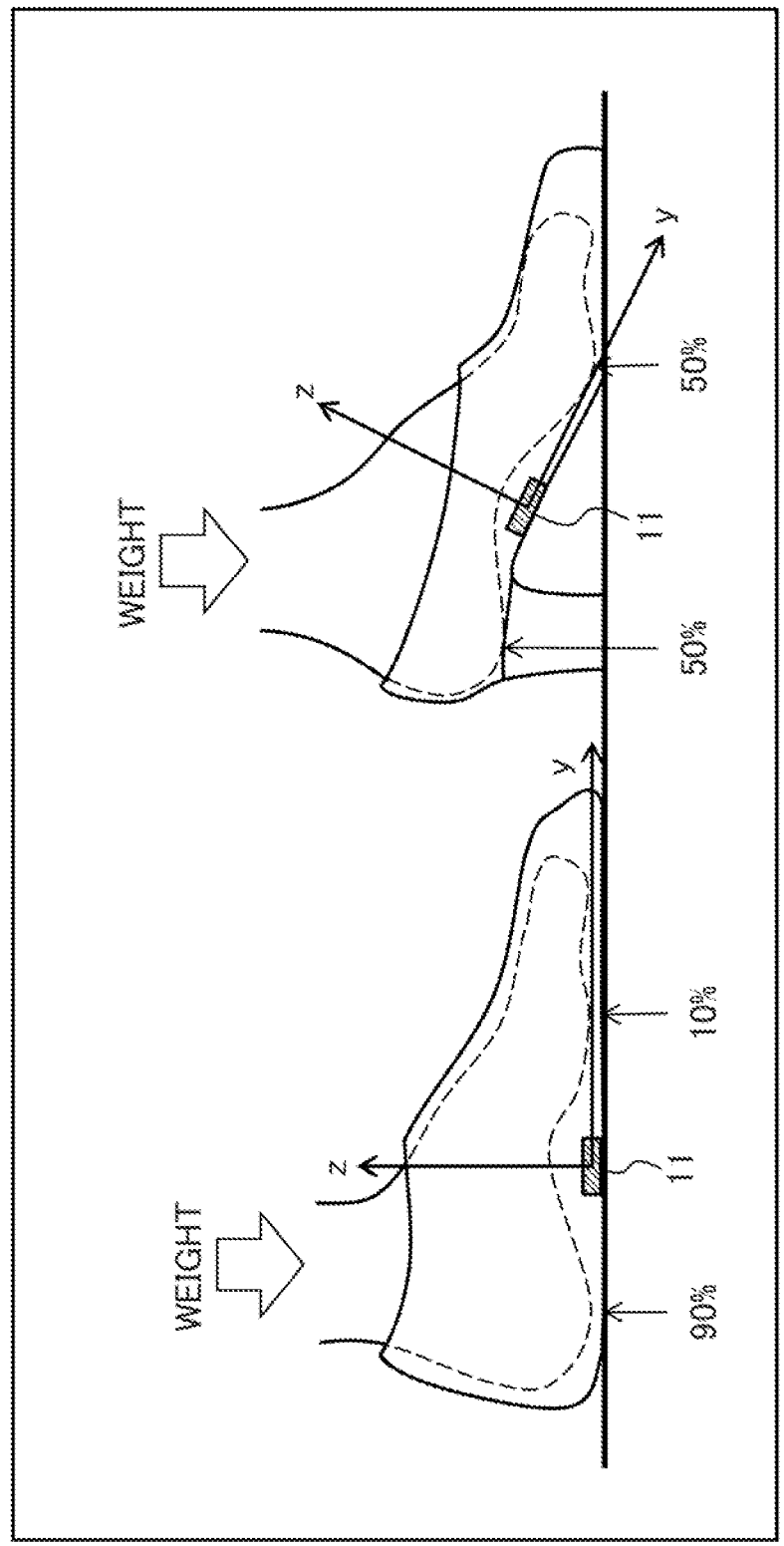
FIG. 5 is a conceptual diagram for describing the local coordinate system when the data acquisition device of the estimation system according to the example embodiment is installed in the footwear.

FIG. 5 is a conceptual diagram for describing a difference in the state of the foot depending on the type of footwear. The left side is an example of wearing footwear with a low heel height, such as an exercise shoe. The right side is an example of wearing footwear with a high heel height, such as an high heel. In the case of the exercise shoe (left side), as an example, a distribution is made in such a way that the ratio of the weight applied to the heel is about 90%, and the ratio of the weight applied to the footrest portion is about 10%. On the other hand, in a high heel or the like, as an example, a distribution is made in such a way that the ratio of the weight applied to the heel is about 50%, and the ratio of the weight applied to the footrest portion is about 50%. That is, when the heel height of the footwear increases, the ratio of the weight applied to the footrest portion increases. When the heel height of the footwear increases, the load applied to the toe side increases, and the load applied to the heel side decreases. Therefore, when the heel height of the footwear increases, the heel joint is in a plantarflexion state in the upright state. Therefore, in the exercise shoe and the high heel, a difference also occurs in the gait mainly due to a difference in the heel height. Since the angle formed between the surface of the sole and the ground in a state where the entire bottom of the footwear is grounded is different in the exercise shoe and the high heel, the initial position of the local coordinates is different. Therefore, the measured data is also different between the case of wearing the exercise shoe and the case of wearing the high heel.

The estimation device 12 acquires sensor data in the local coordinate system from the data acquisition device 11. The estimation device 12 converts the acquired sensor data in the local coordinate system into the world coordinate system to generate time-series data. The estimation device 12 extracts gait waveform data for one gait cycle from the generated time-series data. The estimation device 12 extracts a feature portion from the extracted gait waveform data for one gait cycle.

Figure 6:
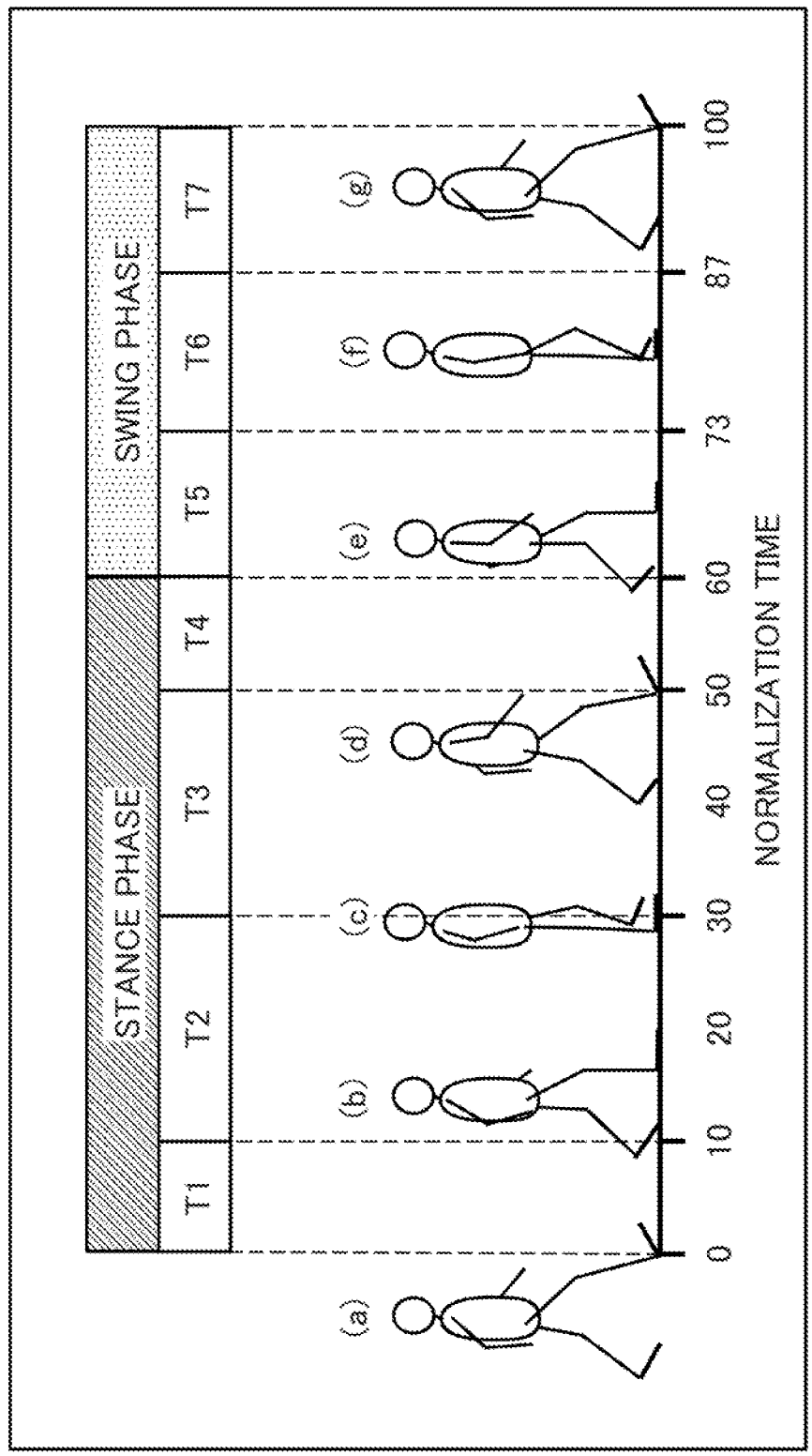
FIG. 6 is a conceptual diagram for describing a general gait cycle.

FIG. 6 is a conceptual diagram for describing a general gait cycle. FIG. 6 illustrates one gait cycle of a right foot. A horizontal axis in FIG. 6 represents a normalized time (also referred to as normalization time) with one gait cycle of the right foot as 100%, with a time point at which the heel of the right foot lands on the ground as a starting point and a time point at which the heel of the right foot next lands on the ground as an ending point. In general, one gait cycle of one foot is roughly divided into a stance phase in which at least a part of the back side of the foot is in contact with the ground and a swing phase in which the back side of the foot is away from the ground. The stance phase is subdivided into an initial stance period T1, a mid-stance period T2, a terminal stance period T3, and a pre-swing period T4. The swing phase is further subdivided into an initial swing period T5, a mid-swing period T6, and a terminal swing period T7.

In FIG. 6, (a) indicates a situation where the heel of the right foot is in contact with the ground (heel grounding). (a) is the starting point of one gait cycle. (b) indicates a situation where the toe of the left foot is separated from the ground in a state where the entire sole of the right foot is in contact with the ground (opposite foot toe separation). (c) indicates a situation where the heel of the right foot is lifted in a state where the entire sole of the right foot is in contact with the ground (heel lift). (d) indicates a situation where the heel of the left foot is in contact with the ground (opposite heel grounding). (e) indicates a situation where the toe of the right foot is separated from the ground in a state where the entire sole of the left foot is in contact with the ground (toe separation). (f) indicates a situation where the left foot and the right foot cross each other in a state where the entire sole of the left foot is grounded (foot crossing). (g) indicates a situation where the heel of the right foot is in contact with the ground (heel grounding). (g) is the ending point of one gait cycle and the starting point of the next gait cycle.

Figure 7:
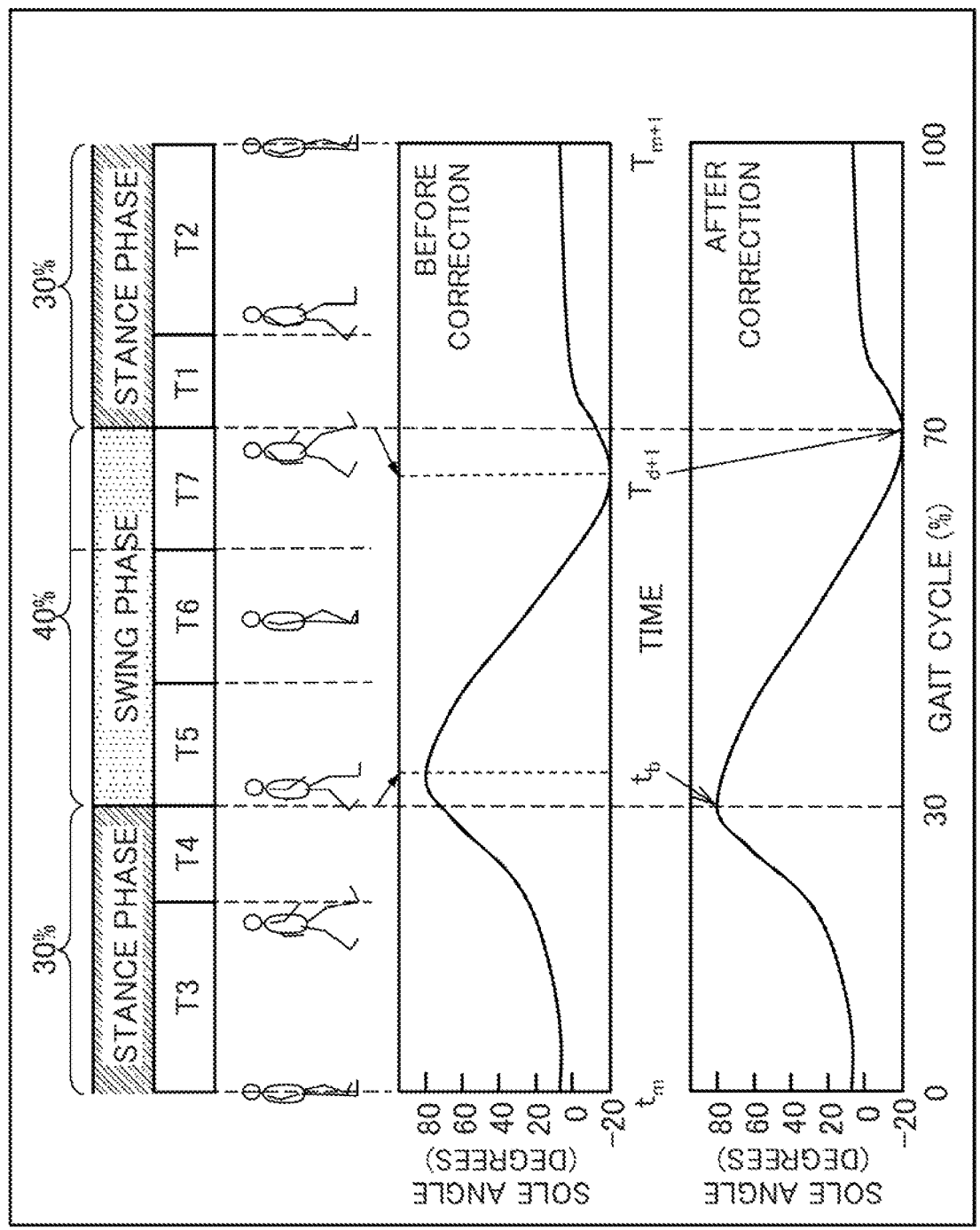
FIG. 7 is a conceptual diagram for describing gait waveform data extracted by an estimation unit of the estimation system according to the example embodiment.

FIG. 7 is a conceptual diagram for describing a relationship between the gait cycle and the time-series data of the sole angle in one gait cycle actually measured. The upper row represents one gait cycle starting from a middle time point $t_m$ in the stance phase and ending at a middle time point $t_{m+1}$ in the next stance phase. The graph of the middle row is time-series data of the sole angle for one walk. The horizontal axis of the graph of the middle row is a time when the sensor data for calculating the sole angle is actually measured, and deviates from the gait cycle of the upper row. In the present example embodiment, the horizontal axis of the time-series data of the sole angle is corrected to match the gait cycle.

The estimation device 12 detects, from the time-series data of the sole angle, a dorsiflexion peak time point to at which the sole angle becomes minimum (dorsiflexion peak) and a plantarflexion peak time point $t_b$ at which the sole angle becomes maximum (plantarflexion peak) next to the dorsiflexion peak. The estimation device 12 detects a dorsiflexion peak time point $t_{d+1}$ of the next dorsiflexion peak of the plantarflexion peak and a plantarflexion peak time point $t_{b+1}$ of the next dorsiflexion peak. The estimation device 12 cuts out the gait waveform data for one gait cycle starting from the time point $t_m$ which is an intermediate point between the dorsiflexion peak time point to and the plantarflexion peak time point $t_b$ and ending at the time point $t_{m+1}$ which is an intermediate point between the dorsiflexion peak time point $t_{d+1}$ and the plantarflexion peak time point $t_{b-1}$. As illustrated in FIG. 7, in the gait waveform data for one gait cycle cut out by the estimation device 12, a maximum (plantarflexion peak) appears at the plantarflexion peak time point $t_b$, and a minimum (dorsiflexion peak) appears at the dorsiflexion peak time point $t_{d+1}$.

The estimation device 12 normalizes the section from the time point $t_m$ to the time point $t_b$ to be 30% of the gait cycle, the section from the time point $t_b$ to the time point $t_{d+1}$ to be 40% of the gait cycle, and the section from the time point $t_{d+1}$ to the time point $t_{m+1}$ to be 30% of the gait cycle. The graph of the lower row is the corrected gait waveform data of the sole angle. The gait waveform data of the sole angle indicates a change in the sole angle with a gait cycle.

Hereinafter, for the time-series data of the spatial acceleration and the spatial angular velocity, similarly to the sole angle, the gait waveform data is illustrated with the horizontal axis corrected to the gait cycle. 30% of the gait cycle corresponds to the timing of the toe separation point in (e) of FIG. 6. 70% of the gait cycle corresponds to the timing of the heel grounding in (a) or (g) of FIG. 6.

The estimation device 12 estimates the footwear worn by the pedestrian by using a learned model obtained by performing machine-learning with the type of the footwear used as a label, and the feature quantity of the feature portion of the gait waveform data obtained when the footwear is worn used as teacher data. The estimation device 12 inputs the feature quantity of the feature portion to the learned model, and estimates the footwear worn by the pedestrian. The estimation device 12 outputs the estimated type of the footwear. The learned model used by the estimation device 12 to estimate the type of footwear will be described later.

The configuration of the estimation system 1 has been described above. The configuration of FIG. 1 is an example, and does not limit the configuration of the estimation system 1 of the present example embodiment.

[Data Acquisition Device]

Figure 8:
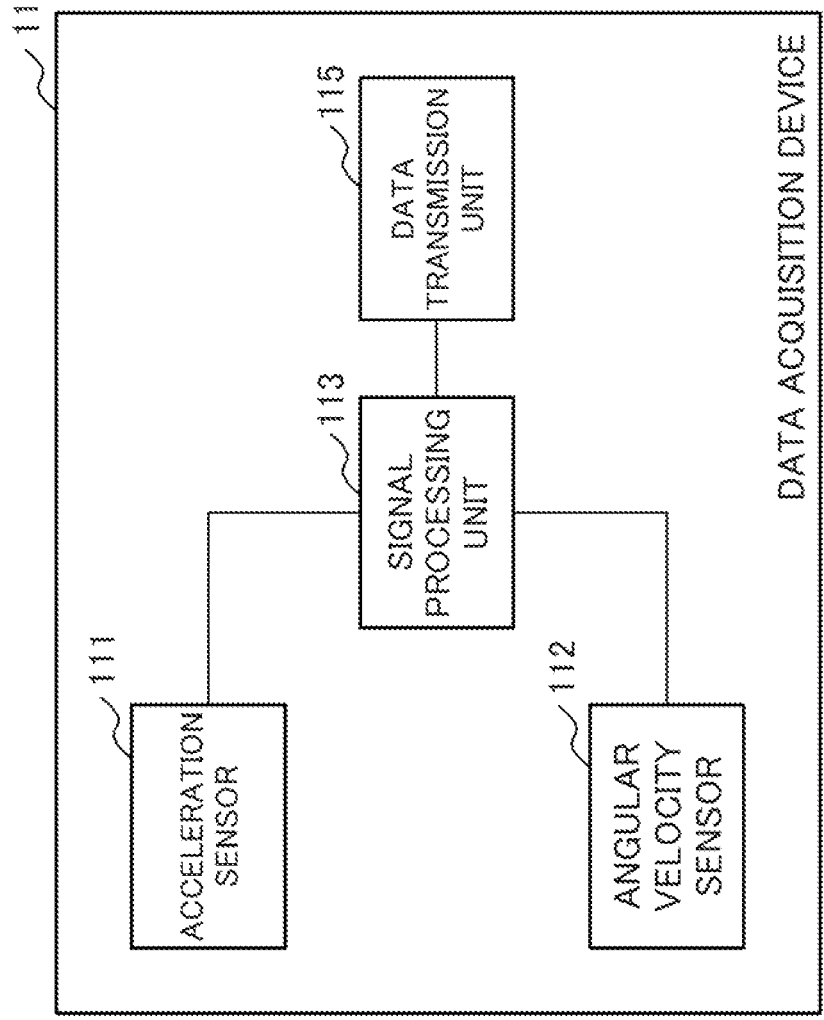
FIG. 8 is a block diagram illustrating an example of a configuration of a data acquisition device of the estimation system according to the example embodiment.

Next, details of the data acquisition device 11 included in the estimation system 1 will be described with reference to the drawings. FIG. 8 is a block diagram illustrating an example of a configuration of the data acquisition device 11. The data acquisition device 11 includes an acceleration sensor 111, an angular velocity sensor 112, a signal processing unit 113, and a data transmission unit 115.

The acceleration sensor 111 is a sensor that measures acceleration in triaxial directions. The acceleration sensor 111 outputs the measured acceleration to the signal processing unit 113.

The angular velocity sensor 112 is a sensor that measures an angular velocity in the triaxial directions. The angular velocity sensor 112 outputs the measured angular velocity to the signal processing unit 113.

The signal processing unit 113 acquires the acceleration and the angular velocity from the acceleration sensor 111 and the angular velocity sensor 112, respectively. The signal processing unit 113 converts the acquired acceleration and angular velocity into digital data, and outputs the converted digital data (also referred to as sensor data) to the data transmission unit 115. The sensor data includes at least acceleration data (including an acceleration vector in the triaxial directions) obtained by converting the acceleration of analog data into the digital data and angular velocity data (including an angular velocity vector in the triaxial directions) obtained by converting the angular velocity of analog data into the digital data. The acceleration data and the angular velocity data are associated with the acquisition times of the acceleration data and the angular velocity data. The signal processing unit 113 may be configured to output sensor data obtained by adding correction such as a mounting error, temperature correction, and linearity correction to the acquired acceleration data and angular velocity data.

The data transmission unit 115 acquires the sensor data from the signal processing unit 113. The data transmission unit 115 transmits the acquired sensor data to the estimation device 12. The data transmission unit 115 may transmit the sensor data to the estimation device 12 via a wire such as a cable, or may transmit the sensor data to the estimation device 12 via wireless communication. For example, the data transmission unit 115 can be configured to transmit the sensor data to the estimation device 12 via a wireless communication function (not illustrated) conforming to a standard such as Bluetooth (registered trademark) or WiFi (registered trademark). The communication function of the data transmission unit 115 may conform to a standard other than Bluetooth (registered trademark) or WiFi (registered trademark).

The configuration of the data acquisition device 11 has been described in detail above. The configuration of FIG. 8 is an example, and does not limit the configuration of the data acquisition device 11 included in the estimation system 1 of the present example embodiment.

[Estimation Device]

Figure 9:
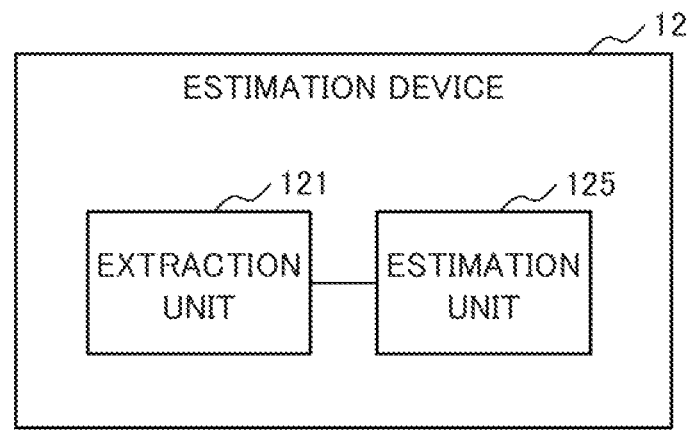
FIG. 9 is a block diagram illustrating an example of a configuration of the estimation device of the estimation system according to the example embodiment.

Next, details of the estimation device 12 included in the estimation system 1 will be described with reference to the drawings. FIG. 9 is a block diagram illustrating an example of a configuration of the estimation device 12. The estimation device 12 includes an extraction unit 121 and an estimation unit 125.

The extraction unit 121 acquires sensor data in the local coordinate system from the data acquisition device 11. For example, the extraction unit 121 acquires three-dimensional acceleration data and angular velocity data in the local coordinate system of the data acquisition device 11. The extraction unit 121 converts the acquired sensor data into the world coordinate system to generate time-series data. For example, the extraction unit 121 generates time-series data of the three-dimensional acceleration data or time-series data of the three-dimensional angular velocity data converted into the world coordinate system.

The extraction unit 121 generates time-series data such as a spatial acceleration and a spatial angular velocity. The extraction unit 121 integrates the spatial acceleration and the spatial angular velocity to generate time-series data of the spatial velocity and the spatial angle (sole angle). The extraction unit 121 generates time-series data at a predetermined timing or time interval set in accordance with a general gait cycle or a gait cycle unique to the user. The timing at which the extraction unit 121 generates the time-series data can be arbitrarily set. For example, the extraction unit 121 continues to generate the time-series data during a period in which walking of the user is continued. The extraction unit 121 may be configured to generate the time-series data for a certain period of time from a specific time point.

The extraction unit 121 extracts time-series data for one gait cycle from the generated time-series data. The extraction unit 121 generates waveform data (hereinafter, referred to as gait waveform data) for one gait cycle in which the time-series data for one gait cycle is made to correspond to a gait cycle. The gait waveform data generated by the extraction unit 121 will be described in detail later.

The extraction unit 121 extracts a feature quantity (gait feature quantity) of a feature portion from the gait waveform data. For example, the extraction unit 121 detects the gait feature quantity from the time-series data of the acceleration in the traveling direction (Y-direction acceleration), the acceleration in the gravity direction (Z-direction acceleration), the angular velocity around the X-axis (roll angular velocity), the angle around the X-axis (roll angle), and the acceleration in the gravity direction (Z-direction acceleration).

The estimation unit 125 stores a learned model obtained by performing machine-learning with the type of footwear used as a label, and the feature quantity of the feature portion of the gait waveform data of the pedestrian wearing the footwear used as teacher data. The estimation unit 125 inputs the gait feature quantity extracted by the extraction unit 121 to the learned model, and estimates the type of the footwear. The estimation unit 125 outputs the estimated type of the footwear. For example, the estimation unit 125 outputs the estimated type of the footwear to a system that distributes content relevant to the type of footwear or an output device such as a display device or a printing device (not illustrated).

Figure 10:
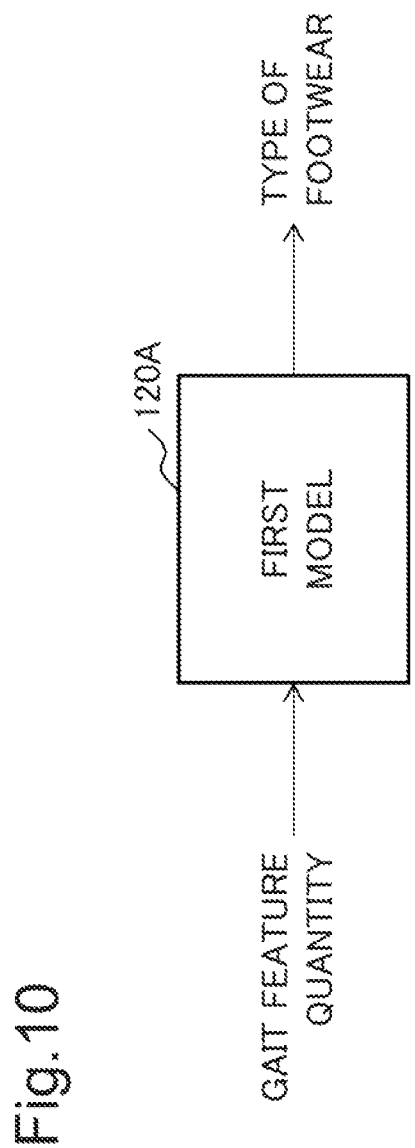
FIG. 10 is a conceptual diagram for describing an example in which the estimation device of the estimation system according to the example embodiment estimates the type of shoe by using a first model.

FIG. 10 is a conceptual diagram illustrating an example in which the gait feature quantity of the gait waveform data is input to a first model 120A obtained by performing machine-learning with the type of footwear used as a label, and the gait feature quantity of the gait waveform data obtained when the footwear is worn used as teacher data. In the example of FIG. 10, when the gait feature quantity is input to the first model 120A, the type of footwear relevant to the gait feature quantity is output. FIG. 10 illustrates an example in which one gait feature quantity is used, but a plurality of gait feature quantities may be used. By using the first model 120A of FIG. 10, for example, it is possible to achieve a service of transmitting the type of footwear to a distribution system which distributes content related to gait and transmitting content relevant to the type of footwear from the distribution system to a terminal of the pedestrian. The content relevant to the type of footwear may be stored in the terminal of the pedestrian or may be received via a network.

Figure 11:
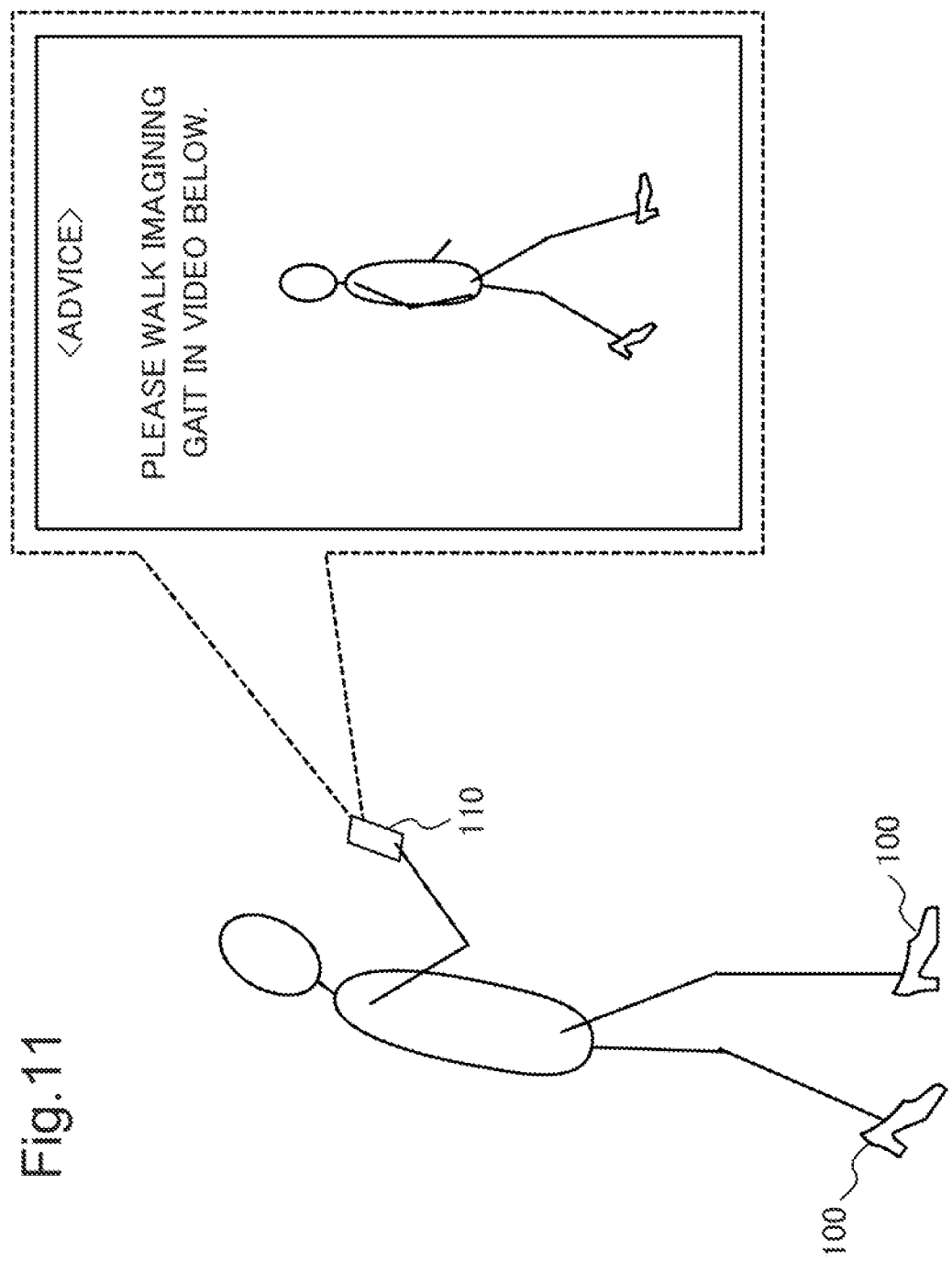
FIG. 11 is a conceptual diagram for describing an example in which the estimation device of the estimation system according to the example embodiment distributes content relevant to the type of shoe.

FIG. 11 illustrates an example in which the content relevant to the type of footwear is displayed on the screen of a mobile terminal 110 of the pedestrian wearing the footwear 100 on which the data acquisition device 11 is installed. However, it is assumed that the mobile terminal 110 includes the estimation device 12. In the example of FIG. 11, the type of the footwear is predicted from the gait feature quantity of the gait waveform data of the pedestrian, and a video moving image including the ideal gait relevant to the type of the footwear is displayed on the mobile terminal 110 of the pedestrian. For example, when the gait of the pedestrian can be measured by using the gait waveform data of the pedestrian, an advice regarding the way of walking and the posture relevant to the type of the footwear may be displayed on the mobile terminal 110 of the pedestrian.

Figure 12:
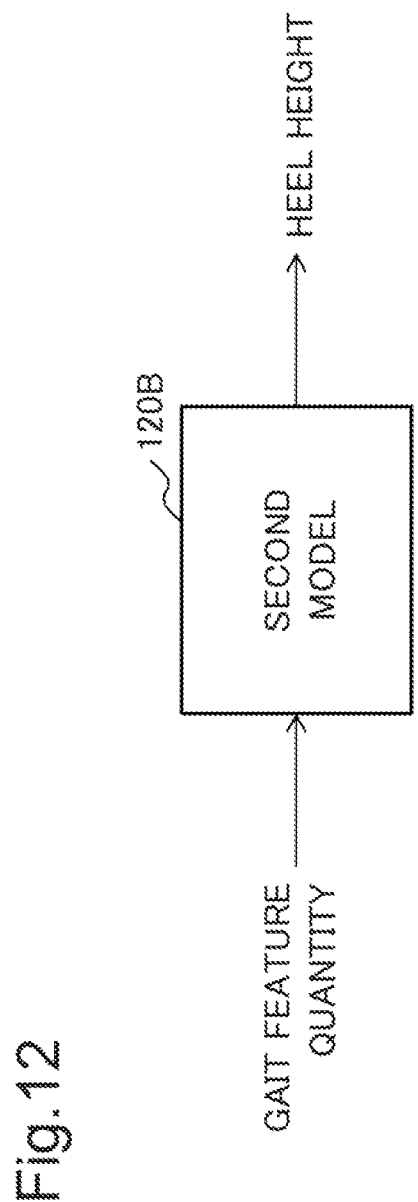
FIG. 12 is a conceptual diagram for describing an example in which the estimation device of the estimation system according to the example embodiment estimates the heel height of the shoe by using a second model.

FIG. 12 is a conceptual diagram illustrating an example in which the gait feature quantity of the gait waveform data for one gait cycle is input to a second model 120B obtained by performing machine-learning with the heel height of the footwear used as a label, and the feature quantity of the feature portion of the gait waveform data obtained when the footwear is worn used as teacher data. In the example of FIG. 12, when the gait feature quantity of the gait waveform data for one gait cycle is input to the second model 120B, the heel height relevant to the gait feature quantity is output. FIG. 12 illustrates an example in which one gait feature quantity is used, but a plurality of gait feature quantities may be used. By using the second model 120B of FIG. 12, for example, it is possible to achieve a service of transmitting the heel height of the footwear to the distribution system which distributes content related to gait and transmitting content relevant to the heel height of footwear from the distribution system to the terminal of the pedestrian. The content relevant to the heel height of footwear may be stored in the terminal of the pedestrian or may be received via a network.

Figure 13:
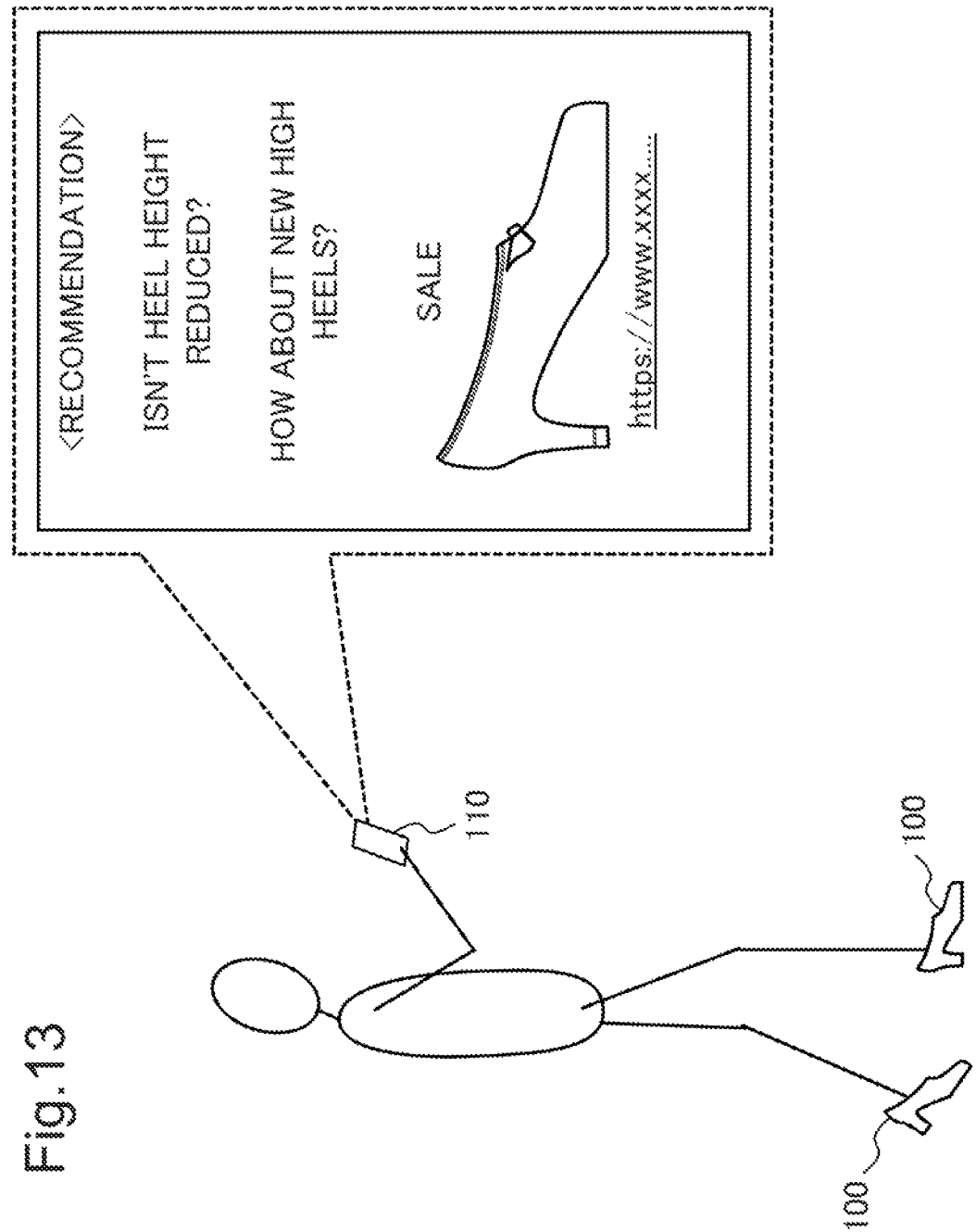
FIG. 13 is a conceptual diagram for describing an example in which the estimation device of the estimation system according to the example embodiment distributes content relevant to the heel height of the shoe.

FIG. 13 illustrates an example in which the content relevant to the heel height of footwear is displayed on the screen of the mobile terminal 110 of the pedestrian wearing the footwear 100 on which the data acquisition device 11 is installed. In the example of FIG. 13, a change in the heel height of the footwear is predicted from the gait feature quantity of the gait waveform data of the pedestrian, and a recommendation relevant to the degree of decrease in the predicted heel height of the footwear is displayed on the screen of the mobile terminal 110 of the pedestrian. For example, the information of a product similar to the footwear worn by the pedestrian according to the degree of decrease in the heel height of the footwear is displayed on the screen of the mobile terminal 110. For example, a link destination to a site where the product can be purchased may be displayed on the screen of the mobile terminal 110.

The configuration of the estimation device 12 has been described in detail above. The configuration of FIG. 9 is an example, and does not limit the configuration of the estimation device 12 included in the estimation system 1 of the present example embodiment.

[Gait Feature Quantity]

Next, the result obtained by collecting 27 subjects and verifying a difference in gait feature quantity depending on the type of footwear will be described. The attributes of the subjects are age of 20s to 50s, height of 150 to 170 centimeters (cm), and weight of 45 to 70 kilograms (kg). As the footwear, exercise shoes having a heel height of 0 cm and high heels having a heel height of 2 cm, 3 cm, or 4.5 cm are used as verification targets. Hereinafter, the type of footwear is distinguished by heel height (0 cm, 2 cm, 3 cm, 4.5 cm).

The data acquisition device 11 is arranged on the back side of the arch of the foot inside any footwear. All the subjects are allowed to walk while wearing each of the above-described four types of footwear, and the gait waveform data is acquired from the sensor data obtained at that time. The following gait waveform data is obtained by averaging, for each subject, the gait waveform data obtained when the subject walks while wearing each of the four types of footwear, and further averaging, for each footwear, the gait waveform data of all the subjects.

In this verification, with reference to the exercise shoes (0 cm), the gait waveform data of each subject is divided into three sets of 2 cm, 3 cm, and 4.5 cm, and a difference from the exercise shoes (0 cm) is taken to extract a feature portion. In this verification, the feature portion satisfying all of the following three conditions (1) to (3) is extracted. A condition for satisfying all of the following three conditions is also referred to as a feature portion extraction condition.

(1) A first condition is that there is a significant difference in the gait waveform data between the 2 cm set and the 3 cm set. Specifically, in each phase (1% increments) in one gait cycle of all the gait waveform data of the 2 cm set and the 3 cm set, a portion where a significant probability p is less than a significant level (0.05) is extracted.

(2) A second condition is that there is a significant difference in the gait waveform data between the 3 cm set and the 4.5 cm set. Specifically, in each phase (1% increments) in one gait cycle of all the gait waveform data of the 3 cm set and the 4.5 cm set, a portion where the significant probability p is less than a significant level (0.05) is extracted.

(3) A third condition is a condition that there is a linear correlation with the change in heel height in the gait waveform data of all sets of 2 cm, 3 cm, and 4.5 cm. Specifically, in each phase (1% increments) in one gait cycle of the gait waveform data of all sets of 2 cm, 3 cm, and 4.5 cm, a portion having a linear correlation with the change in heel height is extracted.

Figure 14:
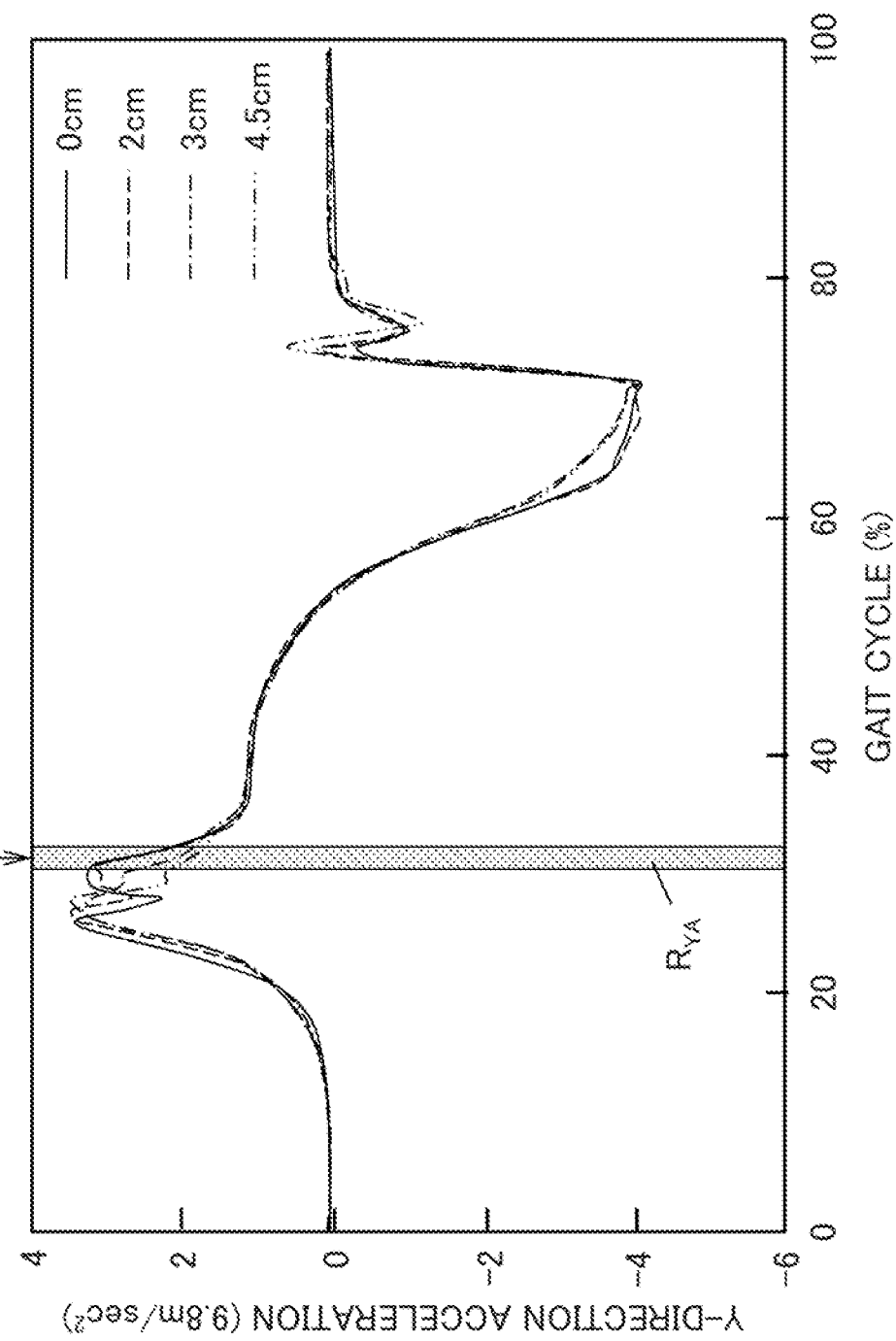
FIG. 14 is a conceptual diagram for describing a feature portion extracted from gait waveform data of Y-direction acceleration by the estimation unit of the estimation system according to the example embodiment.

FIG. 14 is gait waveform data of the acceleration in the traveling direction (Y-direction acceleration) obtained by walking of the subject wearing each footwear of 0 cm, 2 cm, 3 cm, and 4.5 cm. From the gait waveform data of the Y-direction acceleration, a region $R_{YA}$ satisfying the feature portion extraction condition around when the gait cycle exceeded 30% is extracted.

The region $R_{YA}$ is a region including an initial swing period. The initial swing period includes a kicking timing. When the height of the heel of the footwear increases, a kicking force for balancing walking is weakened. Therefore, at the initial swing period, it is estimated that the acceleration in the traveling direction (Y-direction acceleration) decreases when the height of the heel of the footwear increases.

Figure 15:
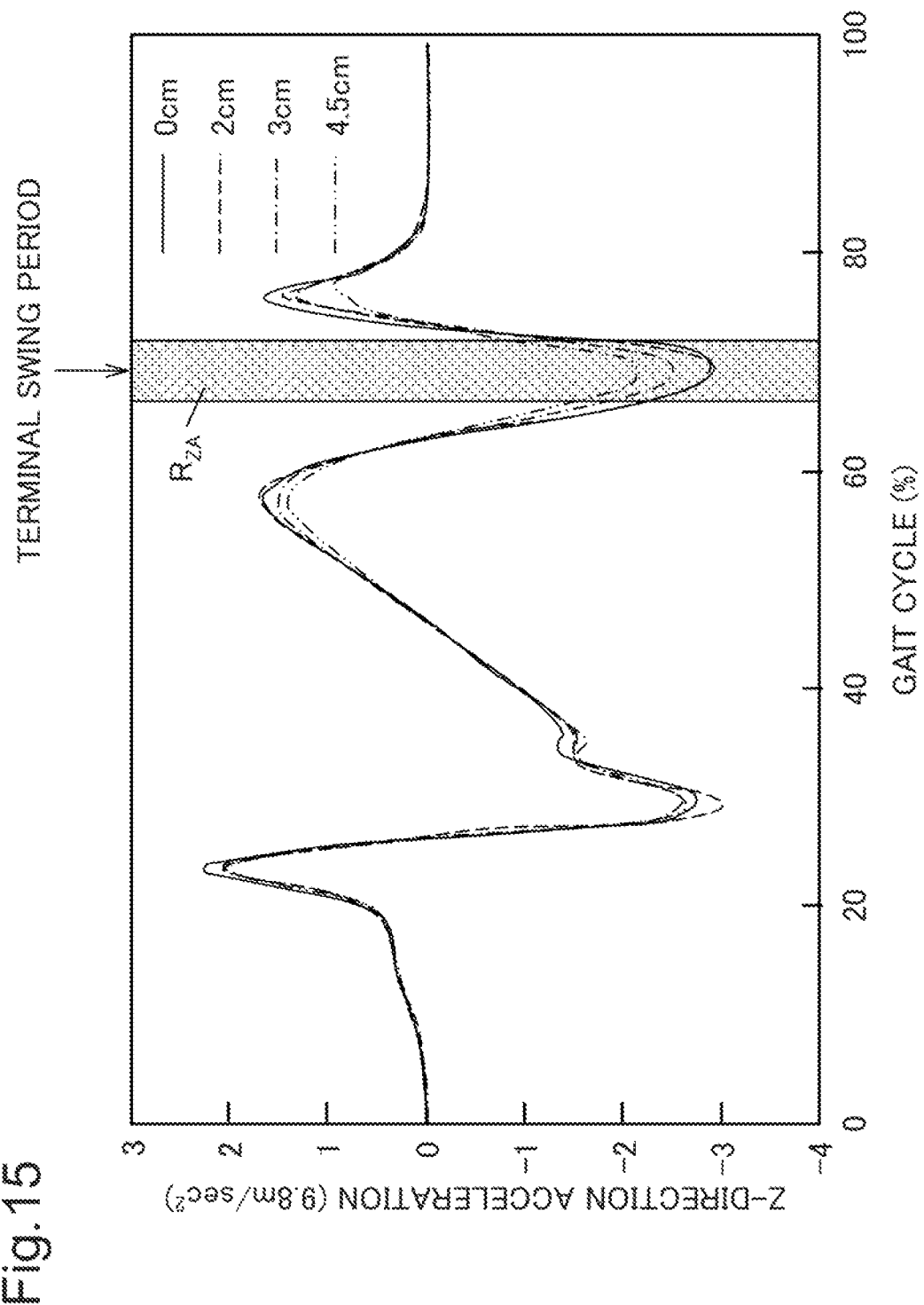
FIG. 15 is a conceptual diagram for describing a feature portion extracted from gait waveform data of Z-direction acceleration by the estimation unit of the estimation system according to the example embodiment.

FIG. 15 is gait waveform data of the acceleration in the gravity direction (Z-direction acceleration) obtained by walking of the subject wearing each footwear of 0 cm, 2 cm, 3 cm, and 4.5 cm. From the gait waveform data of the Z-direction acceleration, a region $R_{ZA}$ satisfying the feature portion extraction condition around 70% of the gait cycle is extracted.

The region $R_{ZA}$ is a region including a terminal swing period. The terminal swing period corresponds to a timing immediately before heel grounding. When the height of the heel of the footwear increases, the range of motion in the gravity direction is reduced, and thus it is estimated that the subject is concerned with instability of the foot at the heel landing and slows the movement of the foot as a compensation operation. Therefore, it is estimated that, at the terminal swing period, when the height of the heel of the footwear increases, the velocity in the gravity direction (Z direction) decreases, and the Z-direction acceleration at the sudden stop at the time of heel grounding decreases.

Figure 16:
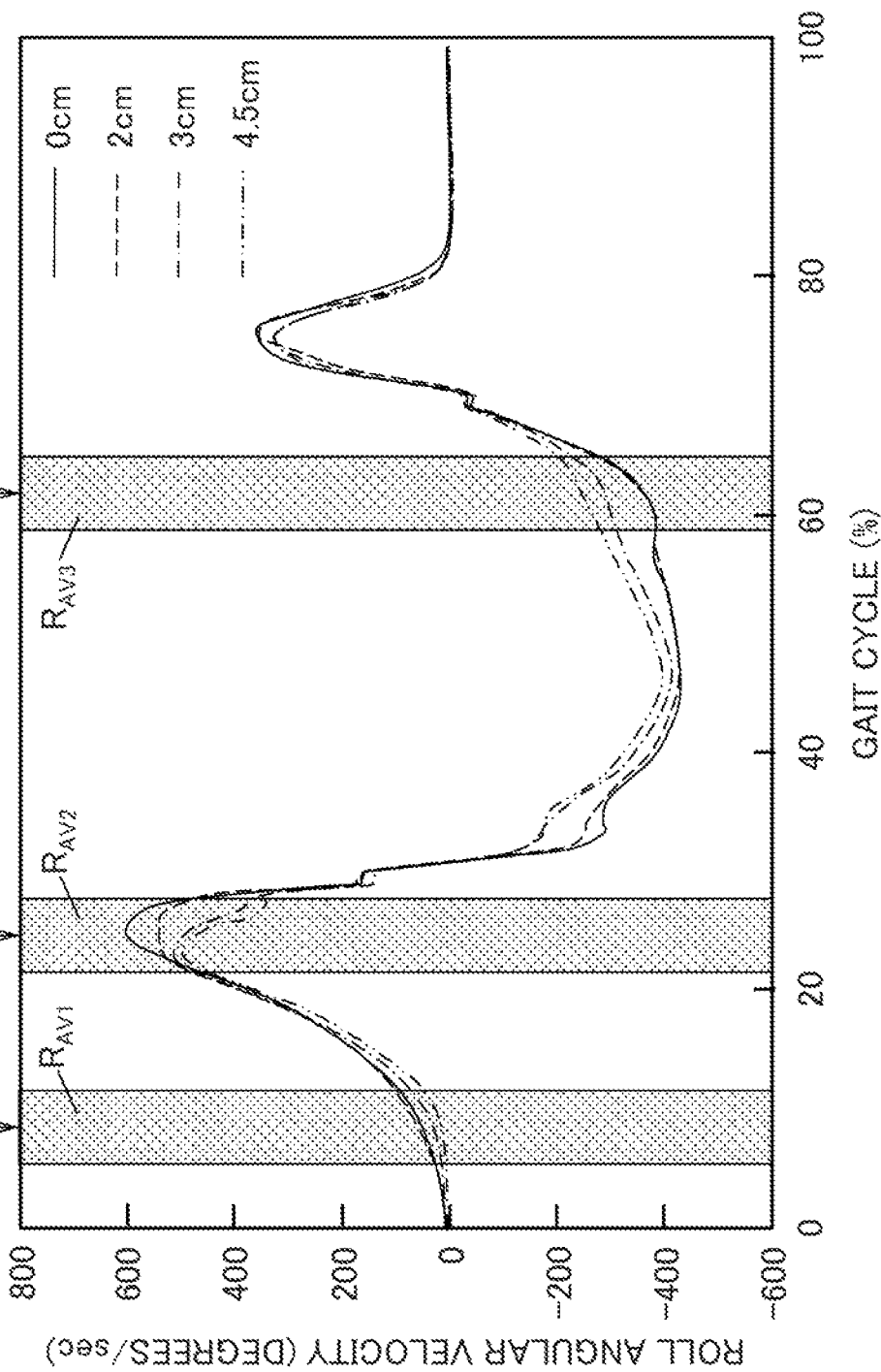
FIG. 16 is a conceptual diagram for describing a feature portion extracted from gait waveform data of a roll angular velocity by the estimation unit of the estimation system according to the example embodiment.

FIG. 16 is gait waveform data of the angular velocity around the X axis (roll angular velocity) obtained by walking of the subject wearing each footwear of 0 cm, 2 cm, 3 cm, and 4.5 cm. From the gait waveform data of the roll angular velocity, three regions (a region $R_{AV1}$, a region $R_{AV2}$, and a region Ravi) satisfying the feature portion extraction condition are extracted.

The region $R_{AV1}$ where the gait cycle is around 10% includes the timing of heel separation. In the gait cycle including the heel separation, the heel joint rotates with the movement of the center of gravity of the sole, and the sole is separated from the ground in the order of the heel, the arch of the foot, the base of the toe, and the toe. When the height of the heel of the footwear increases, the heel and the arch of the foot are separated from the ground from the beginning. Thus, it is estimated that the rotation operation of the heel joint for separating the heel and the arch of the foot from the ground becomes unnecessary, and the angular velocity when the heel joint rotates decreases.

The region $R_{AV2}$ around when the gait cycle exceeds 20% includes the timing of kicking of the foot. When the height of the heel of the footwear increases, the foot is in the plantarflexion state in the upright state, and thus the range of motion of the heel joint is reduced. Therefore, it is estimated that when the height of the heel of the footwear increases, the angular velocity when the heel joint rotates decreases until the plantarflexion angle is maximized in kicking of the foot.

The region $R_{AV3}$ where the gait cycle is around 60% includes the timing of the terminal swing period. When the height of the heel of the footwear increases, the range of motion of the foot is reduced. Therefore, it is estimated that the subject is concerned with instability at the time of heel grounding, and the rotation of the foot is delayed as a compensation operation.

Figure 17:
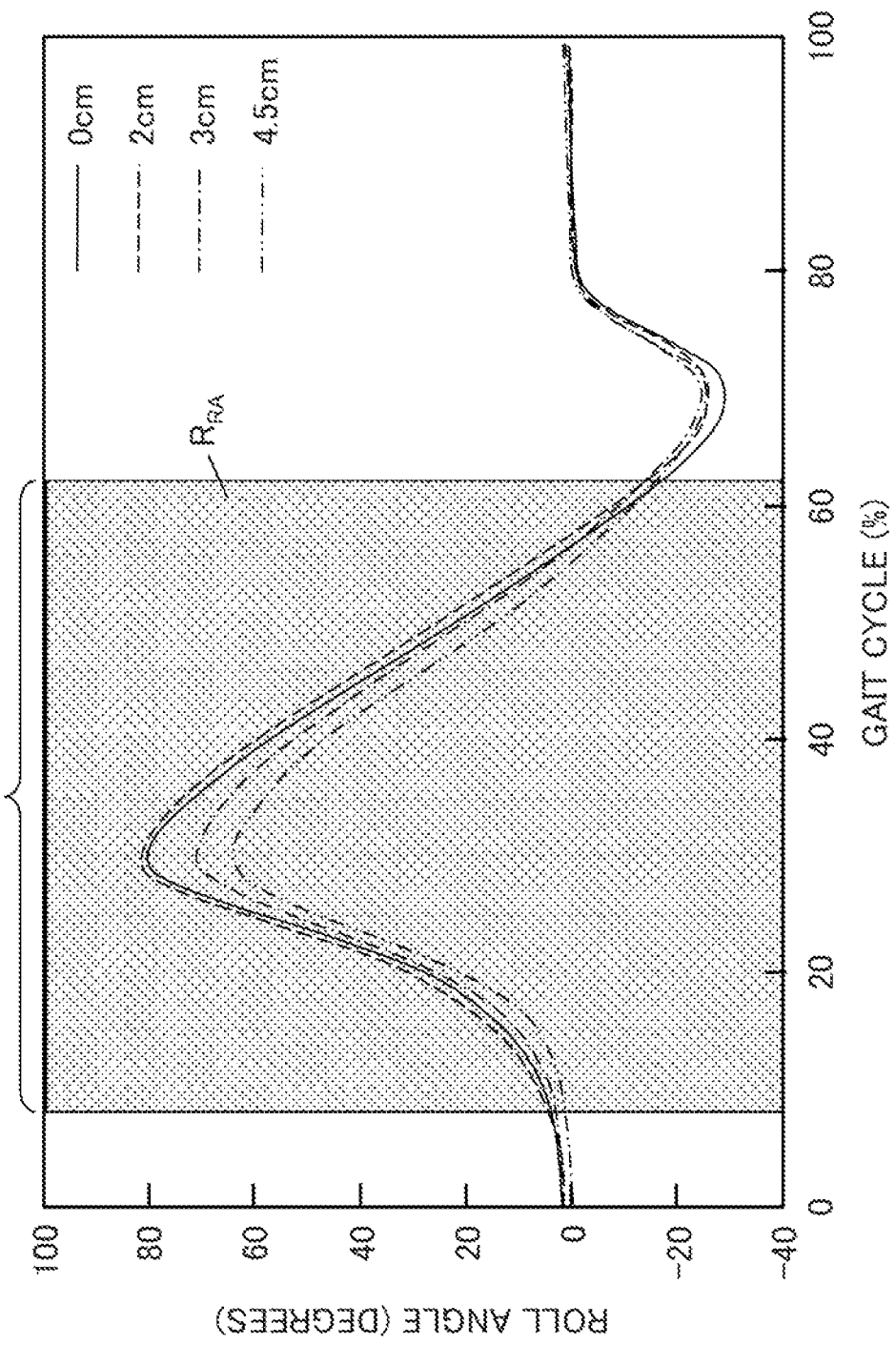
FIG. 17 is a conceptual diagram for describing a feature portion extracted from gait waveform data of a roll angle by the estimation unit of the estimation system according to the example embodiment.

FIG. 17 is gait waveform data of an angle around the X axis (roll angle) obtained by walking of the subject wearing each footwear of 0 cm, 2 cm, 3 cm, and 4.5 cm. The roll angle is calculated by integrating the angular velocity around the X axis (roll angular velocity). Regarding the roll angle, the initial value varies depending on the heel height, and thus the roll angle is offset based on a case where the heel height is 0. From the gait waveform data of the roll angle, a wide region $R_{RA}$ satisfying the feature portion extraction condition is extracted.

The region $R_{RA}$ is a period from the mid-stance period to the terminal swing period. When the height of the heel of the footwear increases, the angle of plantarflexion in the upright state increases, and the range of motion of the heel joint until the angle of plantarflexion is maximized is reduced. Therefore, it is estimated that when the height of the heel of the footwear increases, the roll angle decreases.

Figure 18:
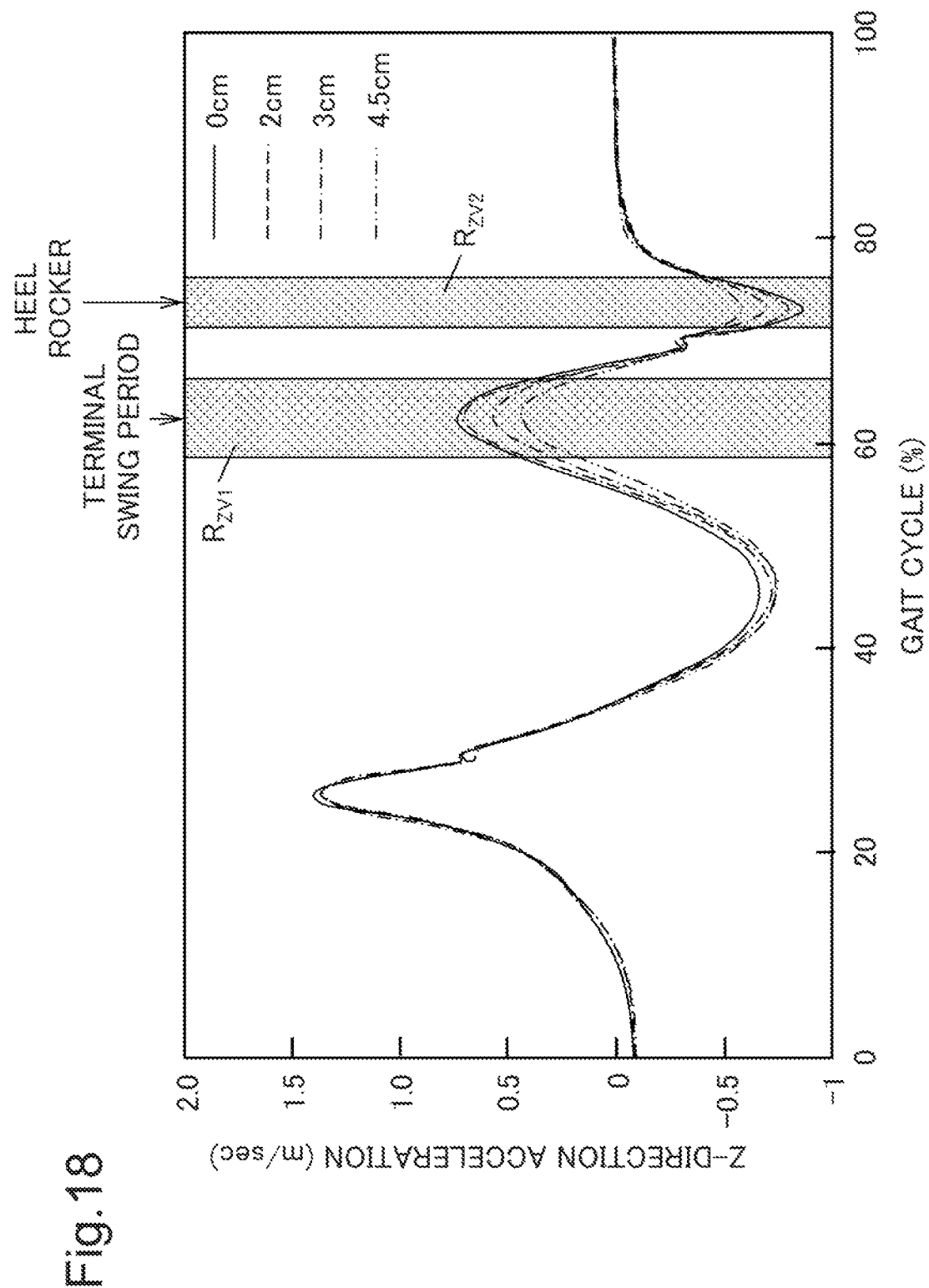
FIG. 18 is a conceptual diagram for describing a feature portion extracted from gait waveform data of a Z-direction velocity by the estimation unit of the estimation system according to the example embodiment.

FIG. 18 is gait waveform data of a velocity in the gravity direction (Z-direction velocity) obtained by walking of the subject wearing each footwear of 0 cm, 2 cm, 3 cm, and 4.5 cm. The Z-direction velocity is calculated by integrating the Z-direction acceleration. From the gait waveform data of the Z-direction velocity, two regions (a region $R_{ZV1}$ and region $R_{ZV2}$) satisfying the feature portion extraction condition are extracted.

The region $R_{ZV1}$ where the gait cycle is around 60% includes the timing of the terminal swing period. When the height of the heel of the footwear increases, the range of motion of the foot is reduced. Therefore, it is estimated that the subject is concerned with instability at the time of heel grounding, and the velocity in the gravity direction (Z direction) decreases as a compensation operation.

The region $R_{ZV2}$ around when the gait cycle exceeds 70% includes the timing of heel rocker. The timing of heel rocker includes a period in which the acceleration in the gravity direction (Z direction) is converted into the traveling direction (Y direction) by the rotation along the outer periphery of the grounded heel after the heel grounding. When the height of the heel of the footwear increases, the range of motion of the foot is reduced. Therefore, it is estimated that the subject is concerned with instability at the time of heel grounding, and the velocity in the gravity direction (Z direction) decreases as a compensation operation.

Next, a verification result will be described which is obtained when the type of the footwear is predicted based on the feature quantity of the feature portion extracted from the gait waveform data of the 27 subjects. The prediction of the type of the footwear is performed by generating a learned model by ten-division cross verification and using the learned model, the learned model being obtained by performing machine-learning with the heel height of the footwear used as a label and the feature quantity of the feature portion of the gait waveform data used as training data. In the machine-learning, a function of a support vector machine (SVM) included in software (MATRAB: registered trademark) manufactured by MathWorks is used.

Figure 19:
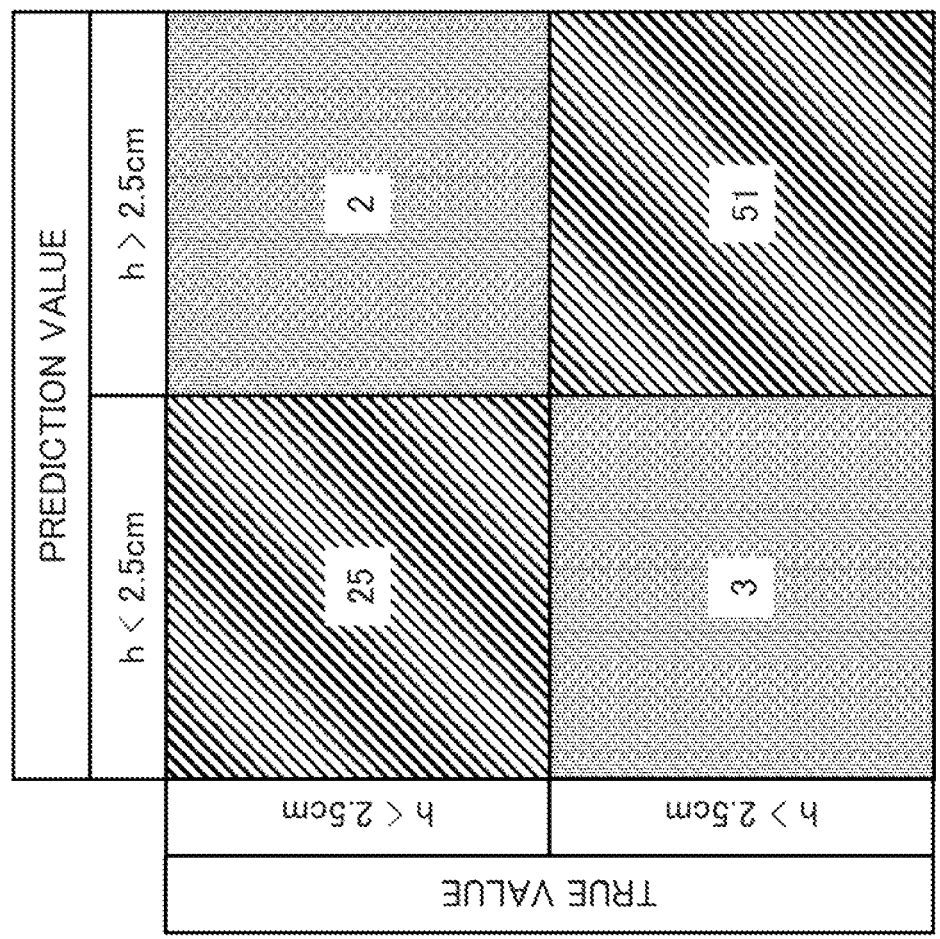
FIG. 19 is an example of a confusion matrix in which a prediction value of a model that has learned a gait feature quantity extracted from gait waveform data of a plurality of subjects is associated with a true value.

FIG. 19 is a confusion matrix when the heel height is classified into a category of sets (a set of 0 cm or 1 cm) lower than 2.5 cm and a category of sets (a set of 2 cm or 4.5 cm) higher than 2.5 cm. In the example of FIG. 19, the true value of the heel height of the footwear coincides with a prediction value with the prediction accuracy equal to or more than 90%.

Figure 20:
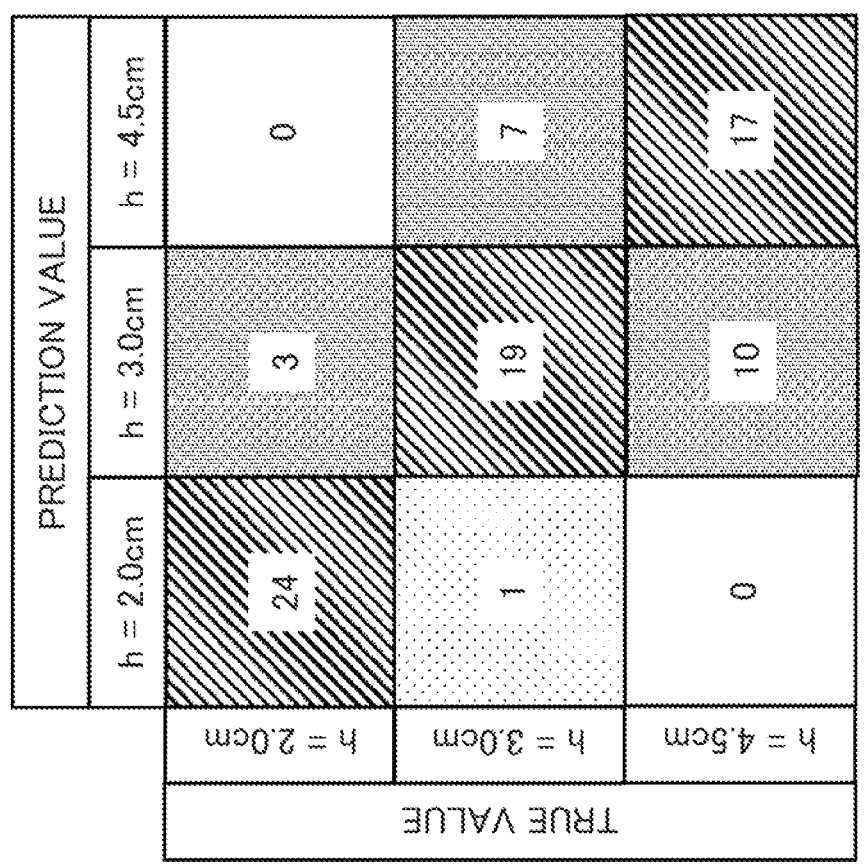
FIG. 20 is another example of the confusion matrix in which the prediction value of the model that has learned the gait feature quantity extracted from the gait waveform data of the plurality of subjects is associated with the true value.

FIG. 20 is a confusion matrix when classified into a category of the set of 2 cm, a category of the set of 3 cm, and a category of the set of 4.5 cm. In the example of FIG. 20, the prediction accuracy of the heel height of the footwear is equal to or more than 70%. Although the prediction accuracy is lower than that of the example of FIG. 19, it is also possible to classify into three sets as illustrated in FIG. 20.

From the verification results of FIGS. 19 and 20, it can be confirmed that when the feature quantity of the feature portion extracted from the gait waveform data satisfies the feature portion extraction condition, the type of the footwear can be predicted by using the learned model in which the feature quantity is machine-learned.

Figure 21:
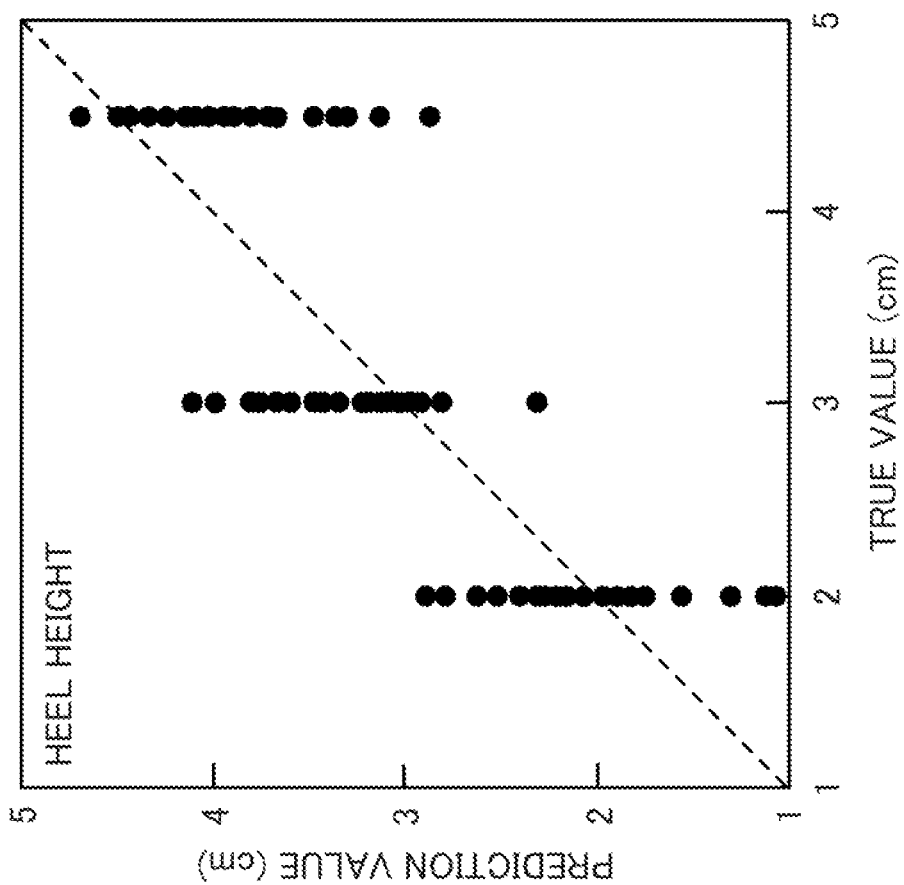
FIG. 21 is a graph for describing a correlation between the prediction value of the model that has learned the gait feature quantity extracted from the gait waveform data of the plurality of subjects and the true value.

FIG. 21 is a graph illustrating a correlation between the prediction value of the heel height of the footwear predicted by using the learned model and the true value of the heel height of the footwear. The root mean squared error (RMSE) of a regression line indicated by a broken line in the graph of FIG. 21 is 0.57. Although the accuracy is not high, it can be confirmed that the heel height of the footwear can be predicted by inputting the feature quantity of the feature portion extracted from the gait waveform data of the pedestrian wearing the footwear having an arbitrary heel height to the learned model.

(Operation)

Next, an operation of the estimation system 1 of the present example embodiment will be described with reference to the drawings. Hereinafter, the extraction unit 121 and the estimation unit 125 of the estimation system 1 are set as the main subjects of operation. The main subject of the operation described below may be the estimation system 1.

[Extraction Unit]

Figure 22:
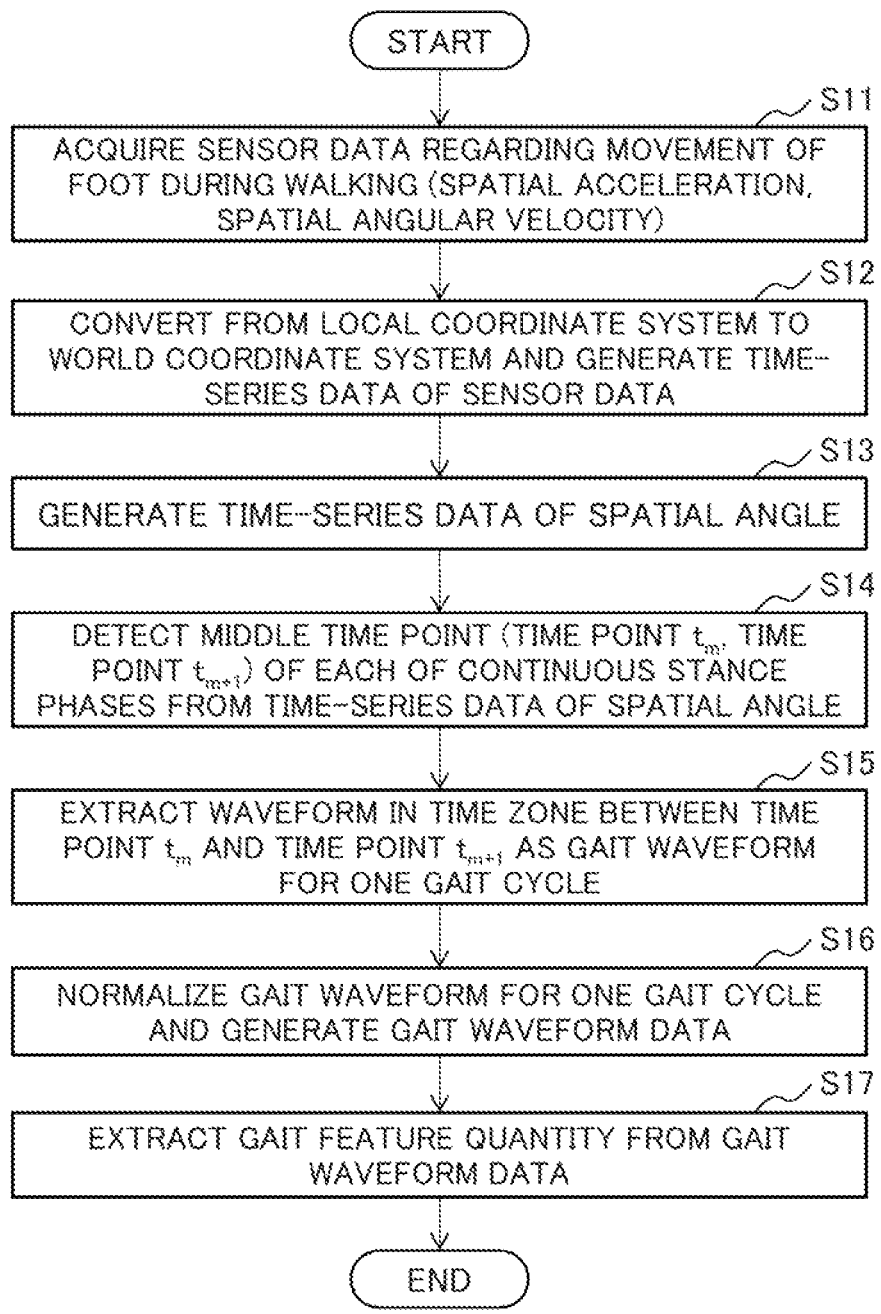
FIG. 22 is a flowchart for describing an example of an operation of an extraction unit of the estimation device of the estimation system according to the example embodiment.

First, an operation of the extraction unit 121 of the estimation system 1 will be described with reference to the drawings. FIG. 22 is a flowchart for explaining an example of the operation of the extraction unit 121.

In FIG. 22, first, the extraction unit 121 acquires, from the data acquisition device 11, sensor data regarding the movement of the foot of the pedestrian walking in the footwear on which the data acquisition device 11 is installed (step S11). The extraction unit 121 acquires the sensor data in the local coordinate system of the data acquisition device 11. For example, the extraction unit 121 acquires a three-dimensional spatial acceleration and a three-dimensional spatial angular velocity from the data acquisition device 11 as the sensor data regarding the movement of the foot.

Next, the extraction unit 121 converts the coordinate system of the acquired sensor data from the local coordinate system to the world coordinate system, and generates time-series data of the sensor data (step S12).

Next, the extraction unit 121 calculates a spatial angle by using at least one of the spatial acceleration and the spatial angular velocity, and generates time-series data of the spatial angle (step S13). The extraction unit 121 generates time-series data of a spatial velocity and a spatial trajectory as necessary. Step S13 may be performed before step S12.

Next, the extraction unit 121 detects a middle time point (time point $t_m$, time point $t_{m+1}$) of each of the continuous stance phases from the time-series data of the spatial angle (step S14).

Next, the extraction unit 121 extracts a waveform in a time zone between the time point $t_m$ and the time point $t_{m+1}$ as a gait waveform for one gait cycle from the time-series data of the spatial acceleration and the spatial angular velocity of the extraction target of the gait feature quantity (step S15).

Next, the extraction unit 121 normalizes the gait waveform for one gait cycle extracted from the time-series data of the spatial acceleration and the spatial angular velocity, and generates gait waveform data (step S16).

Then, the extraction unit 121 extracts the feature quantity (gait feature quantity) of the feature portion from the generated gait waveform data (step S17).

An example of the operation of the extraction unit 121 has been described above. The flowchart of FIG. 22 is an example and does not limit the operation of the extraction unit 121.

[Estimation Unit]

Figure 23:
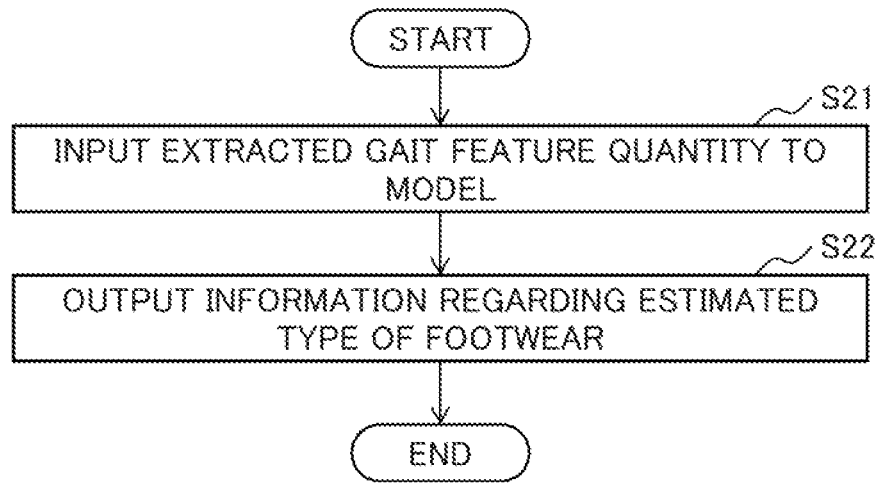
FIG. 23 is a flowchart for describing an example of an operation of the estimation unit of the estimation device of the estimation system according to the example embodiment.

Next, an operation of the estimation unit 125 of the estimation system 1 will be described with reference to the drawings. FIG. 23 is a flowchart for describing an example of the operation of the estimation unit 125.

In FIG. 23, first, the estimation unit 125 inputs the gait feature quantity extracted by the extraction unit 121 to the learned model (step S21).

The estimation unit 125 then outputs information based on the output from the learned model and regarding the type of footwear (step S22).

An example of the operation of the estimation unit 125 has been described above. The flowchart of FIG. 23 is an example and does not limit the operation of the estimation unit 125.

As described above, the estimation system of the present example embodiment includes a data acquisition device and an estimation device. The data acquisition device is installed on footwear. The data acquisition device measures spatial acceleration and a spatial angular velocity. The data acquisition device generates sensor data based on the measured spatial acceleration and spatial angular velocity, and transmits the generated sensor data to the estimation device. The estimation device includes an extraction unit that acquires the sensor data from the sensor installed on the footwear and uses the sensor data to extract a gait feature quantity characteristic of walking in the footwear, and an estimation unit that estimates a type of the footwear based on the gait feature quantity extracted by the extraction unit.

According to the present example embodiment, the sensor data is acquired from the sensor installed in the footwear, the gait feature quantity characteristic of walking in the footwear is extracted by using the sensor data, and the type of footwear can be estimated based on the extracted gait feature quantity.

In one aspect of the present example embodiment, the extraction unit generates time-series data of a gait parameter by using the sensor data and generates gait waveform data by normalizing the time-series data of the gait parameter to a gait cycle. The extraction unit extracts the gait feature quantity characteristic of walking in the footwear from the gait waveform data.

In the present aspect, the gait feature quantity is extracted from the gait waveform data obtained by normalizing the time-series data of the gait parameter to the gait cycle. Therefore, according to the present aspect, it is possible to specify the gait phase from which the gait feature quantity is extracted.

In one aspect of the present example embodiment, the extraction unit generates time-series data of a spatial angle by using the sensor data. The extraction unit detects a middle time point of a stance phase from the time-series data of the spatial angle. The extraction unit extracts waveform data from a time zone between the middle time points of the continuous stance phases in the time-series data of the gait parameter. The extraction unit generates the gait waveform data by normalizing the extracted waveform data to the gait cycle.

In the present aspect, the gait waveform data for one gait cycle with a mid-stance period as a starting point and an ending point is extracted from the time-series data of the gait parameter. Therefore, according to the present aspect, it is possible to more reliably specify the gait phase from which the gait feature quantity is extracted.

In one aspect of the present example embodiment, the extraction unit extracts the characteristic gait feature quantity extracted from the gait waveform data obtained from the time-series data of the gait parameter. For example, the extraction unit extracts the characteristic gait feature quantity in an initial swing period, the gait feature quantity being extracted from the gait waveform data obtained from time-series data of acceleration in a traveling direction of a pedestrian walking in the footwear. For example, the extraction unit extracts the characteristic gait feature quantity in a terminal swing period, the gait feature quantity being extracted from the gait waveform data obtained from time-series data of acceleration in a gravity direction. For example, the extraction unit extracts the characteristic gait feature quantity in at least one of heel separation, kicking, and the terminal swing period, the gait feature quantity being extracted from the gait waveform data obtained from time-series data of an angular velocity around a lateral axis of the pedestrian walking in the footwear. For example, the extraction unit extracts the characteristic gait feature quantity in a period from the mid-stance period to the terminal swing period, the gait feature quantity being extracted from the gait waveform data obtained from time-series data of an angle around the lateral axis of the pedestrian. For example, the estimation unit extracts the characteristic gait feature quantity in at least one of the terminal swing period and a heel rocker, the gait feature quantity being extracted from the gait waveform data obtained from time-series data of a velocity in the gravity direction.

In the present aspect, the characteristic gait feature quantity extracted from the gait waveform data is extracted. Therefore, according to the present aspect, the type of footwear can be more accurately estimated by using the characteristic gait feature quantity extracted from the gait waveform data.

In one aspect of the present example embodiment, the estimation unit estimates the type of the footwear based on the gait feature quantity extracted by the extraction unit by using a first model obtained by machine-learning the gait feature quantity characteristic of walking in the footwear with the type of the footwear used as a label. According to the present aspect, when the gait feature quantity is input to the model generated by machine-learning, the type of the footwear from which the gait feature quantity is extracted can be estimated.

In one aspect of the present example embodiment, the estimation unit estimates a heel height of the footwear based on the gait feature quantity extracted by the extraction unit by using a second model obtained by machine-learning the gait feature quantity characteristic of walking in the footwear with the heel height of the footwear used as a label. According to the present aspect, when the gait feature quantity is input to the model generated by machine-learning, the heel height of the footwear from which the gait feature quantity is extracted can be estimated.

In one aspect of the present example embodiment, the estimation unit outputs distribution information relevant to an estimation result of the type of the footwear. According to the present aspect, the pedestrian can acquire the distribution information relevant to the type of footwear in real time.

(Hardware)

Here, a hardware configuration for executing the processing of the estimation device according to the example embodiment will be described by using the information processing device 90 of FIG. 24 as an example. The information processing device 90 in FIG. 24 is a configuration example for executing the processing of the estimation device of each example embodiment, and does not limit the scope of the present invention.

As illustrated in FIG. 24, the information processing device 90 includes a processor 91, a main storage device 92, an auxiliary storage device 93, an input/output interface 95, and a communication interface 96.

In FIG. 24, the interface is abbreviated as an I/F (interface). The processor 91, the main storage device 92, the auxiliary storage device 93, the input/output interface 95, and the communication interface 96 are data-communicably connected to each other via a bus 99. The processor 91, the main storage device 92, the auxiliary storage device 93, and the input/output interface 95 are connected to a network such as the Internet or an intranet via the communication interface 96.

The processor 91 develops the program stored in the auxiliary storage device 93 or the like in the main storage device 92 and executes the developed program. In the present example embodiment, it is sufficient if the configuration is made to use the software program installed in the information processing device 90. The processor 91 executes processing by the estimation device according to the present example embodiment.

The main storage device 92 has a region in which a program is developed. It is sufficient if the main storage device 92 is a volatile memory such as a dynamic random access memory (DRAM). A nonvolatile memory such as a magnetoresistive random access memory (MRAM) may be configured and added as the main storage device 92.

The auxiliary storage device 93 stores various types of data. The auxiliary storage device 93 includes a local disk such as a hard disk or a flash memory. The various types of data may be stored in the main storage device 92, and the auxiliary storage device 93 may be omitted.

The input/output interface 95 is an interface for connecting the information processing device 90 and a peripheral device. The communication interface 96 is an interface for connecting to the external system or device through a network such as the Internet or an intranet based on a standard or a specification. The input/output interface 95 and the communication interface 96 may be shared as an interface connected to an external device.

An input device such as a keyboard, a mouse, or a touch panel may be configured to be connected to the information processing device 90 as necessary. These input devices are used to input information and settings. In a case where the touch panel is used as the input device, it is sufficient if the display screen of a display device also serves as the interface of the input device. It is sufficient if the data communication between the processor 91 and the input device is mediated by the input/output interface 95.

The information processing device 90 may be provided with a display device for displaying information. In a case where the display device is provided, the information processing device 90 preferably includes a display control device (not illustrated) for controlling the display of the display device. It is sufficient if the display device is connected to the information processing device 90 via the input/output interface 95.

The above is an example of the hardware configuration for enabling the estimation device according to each example embodiment of the present invention. The hardware configuration of FIG. 24 is an example of the hardware configuration for executing arithmetic processing of the estimation device according to each example embodiment, and does not limit the scope of the present invention. A program for causing a computer to execute processing related to the estimation device according to each example embodiment is also included in the scope of the present invention.

A non-transitory recording medium (also referred to as a program recording medium) in which the program according to each example embodiment is recorded is also included in the scope of the present invention. For example, the recording medium can be achieved by, for example, an optical recording medium such as a compact disc (CD) or a digital versatile disc (DVD). The recording medium may be achieved by a semiconductor recording medium such as a universal serial bus (USB) memory or a secure digital (SD) card, a magnetic recording medium such as a flexible disk, or another recording medium.

The components of the estimation device of each example embodiment can be randomly combined. The components of the estimation device of each example embodiment may be achieved by software or may be achieved by a circuit.

While the invention has been particularly shown and described with reference to exemplary embodiments thereof, the invention is not limited to these embodiments. It will be understood by those of ordinary skill in the art that various changes in form and details may be made therein without departing from the spirit and scope of the present invention as defined by the claims.

REFERENCE SIGNS LIST

1 estimation system
11 data acquisition device
12 estimation device
111 acceleration sensor
112 angular velocity sensor
113 signal processing unit
115 data transmission unit
120A first model
120B second model
121 extraction unit
125 estimation unit

What is claimed is:

1. An estimation device comprising:
at least one memory storing instructions; and
at least one processor connected to the at least one memory and configured to execute the instructions to:
acquire sensor data including acceleration and angular velocity from a sensor installed on a footwear worn by a user;
extract a gait feature quantity characteristic of walking in the footwear by using time-series data of the sensor data including the acceleration and the angular velocity;
estimate a heel height of the footwear, the heel height being a relative height of a heel of the footwear with respect to a footrest portion of a sole of the footwear, based on the gait feature quantity characteristic of walking in the footwear by using a second model obtained by machine learning the gait feature quantity characteristic of walking in the footwear with the heel height of the footwear used as a second label;
estimate a type of the footwear, the type of footwear being exercise shoes or high heels, based on the gait feature quantity relevant to a heel height by using a first model obtained by machine learning the gait feature quantity characteristic of walking in the footwear with the heel height of the footwear used as a label of exercise shoes or high heels; and
output data of a video moving image and advice regarding a way of walking and a posture relevant to an ideal gait with the type of the footwear so as to make a decision to improve the walking with the footwear.

2. The estimation device according to claim 1, wherein the at least one processor is configured to execute the instructions to
generate time-series data of a gait parameter by using the sensor data,
generate gait waveform data by normalizing the time-series data of the gait parameter to a gait cycle, and
extract the gait feature quantity characteristic of walking in the footwear from the gait waveform data.

3. The estimation device according to claim 2, wherein the at least one processor is configured to execute the instructions to generate time-series data of a spatial angle by using the sensor data, detect a middle time point of a stance phase from the time-series data of the spatial angle, extract waveform data from a time zone between a middle time point of a preceding stance phase and a middle time point of a subsequent stance phase for continuous stance phases in the time-series data of the gait parameter, and generate the gait waveform data by normalizing the extracted waveform data to the gait cycle.

4. The estimation device according to claim 3, wherein the at least one processor is configured to execute the instructions to extract at least one gait feature quantity of a characteristic gait feature quantity in an initial swing period-extracted from gait waveform data obtained from time-series data of acceleration in a traveling direction of a pedestrian walking in the footwear, a characteristic gait feature quantity in a terminal swing period-extracted from gait waveform data obtained from time-series data of acceleration in a gravity direction, a characteristic gait feature quantity in at least one of heel separation, kicking, and the terminal swing period-extracted from gait waveform data obtained from time-series data of an angular velocity around a lateral axis of the pedestrian walking in the footwear, a characteristic gait feature quantity in a period from a mid-stance period to the terminal swing period extracted from gait waveform data obtained from time-series data of an angle around the lateral axis of the pedestrian, and a characteristic gait feature quantity in at least one of the terminal swing period and a heel rocker extracted from gait waveform data obtained from time-series data of a velocity in the gravity direction.

5. The estimation device according to claim 1, wherein the at least one processor is configured to execute the instructions to estimate a heel height of the footwear based on the gait feature quantity by using a second model obtained by machine learning the gait feature quantity characteristic of walking in the footwear with the heel height of the footwear used as a label.

6. An estimation system comprising:
the estimation device according to claim 1; and
a data acquisition device that is installed on the footwear, measures a spatial acceleration and a spatial angular velocity, generates the sensor data based on the measured spatial acceleration and spatial angular velocity, and transmits the generated sensor data to the estimation device.

7. An estimation method performed by a computer, the method comprising:
acquiring sensor data including acceleration and angular velocity from a sensor installed on a footwear worn by a user;

extracting a gait feature quantity characteristic of walking in the footwear by using time-series data of the sensor data including the acceleration and the angular velocity;

estimating a heel height of the footwear, the heel height being a relative height of a heel of the footwear with respect to a footrest portion of a sole of the footwear, based on the gait feature quantity characteristic of walking in the footwear by using a second model obtained by machine learning the gait feature quantity characteristic of walking in the footwear with the heel height of the footwear used as a second label;

estimating a type of the footwear, the type of footwear being exercise shoes or high heels, based on the extracted gait feature quantity relevant to a heel height by using a first model obtained by machine learning the gait feature quantity characteristic of walking in the footwear with the heel height of the footwear used as a label of exercise shoes or high heels; and outputting data of a video moving image and advice regarding a way of walking and a posture relevant an ideal gait with to the type of the footwear so as to make a decision to improve the walking with the footwear.

8. A non-transitory program recording medium having stored therein a program causing a computer to execute a process comprising:
acquiring sensor data including acceleration and angular velocity from a sensor installed on a footwear worn by a user;

extracting a gait feature quantity characteristic of walking in the footwear by using time-series data of the sensor data including the acceleration and the angular velocity;

estimating a heel height of the footwear, the heel height being a relative height of a heel of the footwear with respect to a footrest portion of a sole of the footwear, based on the gait feature quantity characteristic of walking in the footwear by using a second model obtained by machine learning the gait feature quantity characteristic of walking in the footwear with the heel height of the footwear used as a second label;

estimating a type of the footwear, the type of footwear being exercise shoes or high heels, based on the extracted gait feature quantity relevant to a heel height by using a first model obtained by machine learning the gait feature quantity characteristic of walking in the footwear with the heel height of the footwear used as a label of exercise shoes or high heels; and outputting data of a video moving image and advice regarding a way of walking and a posture relevant an ideal gait with to the type of the footwear so as to make a decision to improve the walking with the footwear.

9. The estimation device according to claim 1, wherein the at least one processor is configured to execute the instructions to predict a change in the heel height over time.

* * * * *